United States Patent
Dagland et al.

(10) Patent No.: US 9,194,007 B2
(45) Date of Patent: Nov. 24, 2015

(54) DOUBLE-STRANDED PROBES FOR THE FLUORESCENT DETECTION OF NUCLEIC ACIDS

(75) Inventors: Typhaine Dagland, Vaucresson (FR); Francois Rieunier, Bois D'arcy (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 484 days.

(21) Appl. No.: 12/445,099

(22) PCT Filed: Oct. 12, 2007

(86) PCT No.: PCT/IB2007/003029
§ 371 (c)(1),
(2), (4) Date: Dec. 4, 2009

(87) PCT Pub. No.: WO2008/044129
PCT Pub. Date: Apr. 17, 2008

(65) Prior Publication Data
US 2011/0129824 A1    Jun. 2, 2011

(30) Foreign Application Priority Data
Oct. 12, 2006    (EP) .................................. 06 291594

(51) Int. Cl.
*C07H 21/04*    (2006.01)
*G01N 33/542*    (2006.01)
(Continued)

(52) U.S. Cl.
CPC ............. *C12Q 1/706* (2013.01); *C12Q 1/6818* (2013.01); *C12Q 1/6844* (2013.01); *C12Q 1/703* (2013.01)

(58) Field of Classification Search
CPC ........... C12Q 1/6818; C12Q 2525/161; C12Q 2537/161; C12Q 2565/525; C12Q 1/706; C12Q 1/6844; C12Q 1/703

USPC ............. 435/6, 7.1, 286.1, 287.2, 288.7, 164, 435/973, 78; 436/537, 546, 800, 805, 172, 436/164, 501; 536/24.3
See application file for complete search history.

(56) References Cited

U.S. PATENT DOCUMENTS 5,030,557 A * 7/1991 Hogan et al. ...................... 435/6
5,710,264 A * 1/1998 Urdea et al. ................. 536/23.1
(Continued)

FOREIGN PATENT DOCUMENTS

EP           1586662      10/2005
WO         WO-9513399     5/1995
(Continued)

OTHER PUBLICATIONS

GenBank entry AF324106.1 (Apr. 19, 2005).*
(Continued)

*Primary Examiner* — Robert T. Crow
*Assistant Examiner* — Joseph G Dauner
(74) *Attorney, Agent, or Firm* — Merchant & Gould P.C.

(57) ABSTRACT

The present invention relates to a double-stranded probe intended for the fluorescent detection of at least one single-stranded or double-stranded target nucleic acid, comprising: —a first strand of formula X1-(L1)a-S1-S'1-(L'1)b-Y1 intended for the detection of a first strand of the target nucleic acid which comprises a sequence of formula T'1-T1; —a second strand of formula X2-(L2)c-S2-S'2-(L'2)d-Y2 intended for the detection of a second strand of the target nucleic acid, if present, the second strand of the target nucleic acid comprising a sequence of formula T'2-T2; wherein two of X1, X2, Y1, and Y2 represent a fluorescent donor, while the two others represent a fluorescent acceptor, and X1 and Y2 can not both represent a fluorescent donor.

14 Claims, 4 Drawing Sheets

(51) Int. Cl.
| | | |
|---|---|---|
| *G01N 33/533* | (2006.01) | |
| *G01N 33/53* | (2006.01) | |
| *G01N 21/76* | (2006.01) | |
| *G01N 21/00* | (2006.01) | |
| *G01N 33/566* | (2006.01) | |
| *C12Q 1/68* | (2006.01) | |
| *C12M 1/36* | (2006.01) | |
| *C12M 1/34* | (2006.01) | |
| *C12P 7/12* | (2006.01) | |
| *C12Q 1/70* | (2006.01) | |

(56) References Cited

U.S. PATENT DOCUMENTS

| | | | | |
|---|---|---|---|---|
| 5,824,795 | A * | 10/1998 | Popoff et al. | 536/24.3 |
| 5,928,862 | A * | 7/1999 | Morrison | 435/6.18 |
| 6,593,091 | B2 * | 7/2003 | Keys et al. | 435/6.11 |
| 2003/0003486 | A1 * | 1/2003 | Sauer et al. | 435/6 |

FOREIGN PATENT DOCUMENTS

| | | |
|---|---|---|
| WO | WO-9940226 | 8/1999 |
| WO | WO-9949293 | 9/1999 |
| WO | WO-0230946 | 4/2002 |

OTHER PUBLICATIONS

GenBank entry AY161141.1 (Jan. 2, 2003).*
GenBank X80892.1 (Apr. 18, 2005).*
Buck et al. Biotechniques. 1999. 27(3): 528-536.*
Nanopore Analysis of DNA Molecules. Center for Biomolecular Science & Engineering. 2009.*
ChemSpider: 4-(4-dimethylaminophenylazo)benzoic acid (retrieved on May 3, 2012 from the internet: <url: http://www.chemspider.com/Chemical-Structure.21231.html>).*
Marras. Nucleic Acids Research. 2002. 30(21): e122.*
Mignet. Nucleic Acids Research. 1998. 26(2): 431-438.*

* cited by examiner

SEQUENCE LISTING

<160> NUMBER OF SEQ ID NOS: 92

<210> SEQ ID NO 1
<211> LENGTH: 35
<212> TYPE: DNA
<213> ORGANISM: Artificial Sequence
<220> FEATURE:
<223> OTHER INFORMATION: Probe for the detection of HBV genome

<400> SEQUENCE: 1
tgcgccgagg gagttcttct tctagggggac gcgca                    35

<210> SEQ ID NO 2
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 2
ttttggagtt cttcttctag gggacc                               26

<210> SEQ ID NO 3
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 3
ttttccctag aagaagaact ccctcg                               26

<210> SEQ ID NO 4
<211> LENGTH: 23
<212> TYPE: DNA
<213> ORGANISM: Artificial Sequence
<220> FEATURE:
<223> OTHER INFORMATION: PCR primer

<400> SEQUENCE: 4
ccaccaaatg cccctatctt atc                                  23

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
gagattgaga tcttctgcga cg                                   22

<210> SEQ ID NO 6
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 6 tttttttggga gttcttcttc tagggg                              26

<210> SEQ ID NO 7
<211> LENGTH: 26
<212> TYPE: DNA
<213> ORGANISM: Artificial Sequence

```
<220> FEATURE:
<223> OTHER INFORMATION: Probe for the detection of HBV genome

<400> SEQUENCE: 7 tttttttgaag aagaactccc tcgcct                                         26

<210> SEQ ID NO 8
<211> LENGTH: 32
<212> TYPE: DNA
<213> ORGANISM: Artificial Sequence
<220> FEATURE:
<223> OTHER INFORMATION: Probe for the detection of HBV genome

<400> SEQUENCE: 8
cggcaggagt ccgcgtaaag agaggtgtgc cg                                   32

<210> SEQ ID NO 9
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 9 tttttttctct ttacgcggac tccccg                                         26

<210> SEQ ID NO 10
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 10 tttttttgtcc gcgtaaagag aggtgc                                         26

<210> SEQ ID NO 11
<211> LENGTH: 18
<212> TYPE: DNA
<213> ORGANISM: Artificial Sequence
<220> FEATURE:
<223> OTHER INFORMATION: PCR primer

<400> SEQUENCE: 11
gctgaatccc gcggacga                                                   18

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
gtgcagaggt gaagcgaagt g                                               21

<210> SEQ ID NO 13
<211> LENGTH: 34
<212> TYPE: DNA
<213> ORGANISM: Artificial Sequence
<220> FEATURE:
<223> OTHER INFORMATION: Probe for the detection of an internal control

<400> SEQUENCE: 13
tgctgcgtcc tccgccgcca ccgcttgggc agca                                 34
```

<210> SEQ ID NO 14
<211> LENGTH: 26
<212> TYPE: DNA
<213> ORGANISM: Artificial Sequence
<220> FEATURE:
<223> OTHER INFORMATION: Probe for the detection of an internal control

<400> SEQUENCE: 14 tttttttaagc ggtggcggcg gaggac                                          26

<210> SEQ ID NO 15
<211> LENGTH: 26
<212> TYPE: DNA
<213> ORGANISM: Artificial Sequence
<220> FEATURE:
<223> OTHER INFORMATION: Probe for the detection of an internal control

<400> SEQUENCE: 15 tttttttcgcc gccaccgctt ggcgat                                          26

<210> SEQ ID NO 16
<211> LENGTH: 19
<212> TYPE: DNA
<213> ORGANISM: Artificial Sequence
<220> FEATURE:
<223> OTHER INFORMATION: PCR primer

<400> SEQUENCE: 16
gagccgcaga tccgagcta                                                   19

<210> SEQ ID NO 17
<211> LENGTH: 22
<212> TYPE: DNA
<213> ORGANISM: Artificial Sequence
<220> FEATURE:
<223> OTHER INFORMATION: PCR primer

<400> SEQUENCE: 17
ggagtggaac atagccgtgg tc                                               22

<210> SEQ ID NO 18
<211> LENGTH: 20
<212> TYPE: DNA
<213> ORGANISM: Artificial Sequence
<220> FEATURE:
<223> OTHER INFORMATION: PCR primers

<400> SEQUENCE: 18
tgccatcgct gtgctacaac                                                  20

<210> SEQ ID NO 19
<211> LENGTH: 20
<212> TYPE: DNA
<213> ORGANISM: Artificial Sequence
<220> FEATURE:
<223> OTHER INFORMATION: PCR primers

<400> SEQUENCE: 19
aacgacggga aggagggtgc                                                  20

<210> SEQ ID NO 20
<211> LENGTH: 35
<212> TYPE: DNA
<213> ORGANISM: Artificial Sequence
<220> FEATURE:
<223> OTHER INFORMATION: Probe for the detection of HIV

```
<400> SEQUENCE: 20
cgcgcatagt ggccagctgt gataaatgtc gcgcg                        35

<210> SEQ ID NO 21
<211> LENGTH: 35
<212> TYPE: DNA
<213> ORGANISM: Artificial Sequence
<220> FEATURE:
<223> OTHER INFORMATION: Probe for the detection of HIV

<400> SEQUENCE: 21
cgcgcatagt agcttgctgt gataaatgtc gcgcg                        35

<210> SEQ ID NO 22
<211> LENGTH: 35
<212> TYPE: DNA
<213> ORGANISM: Artificial Sequence
<220> FEATURE:
<223> OTHER INFORMATION: Probe for the detection of HIV

<400> SEQUENCE: 22
cgcgcatagt agccaactgt gataaatgtc gcgcg                        35

<210> SEQ ID NO 23
<211> LENGTH: 24
<212> TYPE: DNA
<213> ORGANISM: Artificial Sequence
<220> FEATURE:
<223> OTHER INFORMATION: Probe for the detection of HIV

<400> SEQUENCE: 23
ttttccagct gtgataaatg tcag                                    24

<210> SEQ ID NO 24
<211> LENGTH: 24
<212> TYPE: DNA
<213> ORGANISM: Artificial Sequence
<220> FEATURE:
<223> OTHER INFORMATION: Probe for the detection of HIV

<400> SEQUENCE: 24
ttttcattta tcacagctgg ctac                                    24

<210> SEQ ID NO 25
<211> LENGTH: 23
<212> TYPE: DNA
<213> ORGANISM: Artificial Sequence
<220> FEATURE:
<223> OTHER INFORMATION: PCR primer

<400> SEQUENCE: 25
aattggagag caatggctag tga                                     23

<210> SEQ ID NO 26
<211> LENGTH: 22
<212> TYPE: DNA
<213> ORGANISM: Artificial Sequence
<220> FEATURE:
<223> OTHER INFORMATION: PCR primer

<400> SEQUENCE: 26
tgtgtacaat ctaattgcca ta                                      22

<210> SEQ ID NO 27
```

```
<211> LENGTH: 45
<212> TYPE: DNA
<213> ORGANISM: Artificial Sequence
<220> FEATURE:
<223> OTHER INFORMATION: Probe for the detection of HIV

<400> SEQUENCE: 27
cgcgcaagtc tacctgacca tgaattgctt cccctttat gcgcg                             45

<210> SEQ ID NO 28
<211> LENGTH: 26
<212> TYPE: DNA
<213> ORGANISM: Artificial Sequence
<220> FEATURE:
<223> OTHER INFORMATION: Probe for the detection of HIV

<400> SEQUENCE: 28
ttttctgacc atgaattgct tcccct                                                 26

<210> SEQ ID NO 29
<211> LENGTH: 26
<212> TYPE: DNA
<213> ORGANISM: Artificial Sequence
<220> FEATURE:
<223> OTHER INFORMATION: Probe for the detection of HIV

<400> SEQUENCE: 29
ttttgaagca attcatggtc aggtag                                                 26

<210> SEQ ID NO 30
<211> LENGTH: 22
<212> TYPE: DNA
<213> ORGANISM: Artificial Sequence
<220> FEATURE:
<223> OTHER INFORMATION: PCR primer

<400> SEQUENCE: 30
tgtgtacaat ctatttgcca ta                                                     22

<210> SEQ ID NO 31
<211> LENGTH: 30
<212> TYPE: DNA
<213> ORGANISM: Artificial Sequence
<220> FEATURE:
<223> OTHER INFORMATION: HBV genome fragment

<400> SEQUENCE: 31
cacctctctt tacgcggact ccccgtctgt                                             30

<210> SEQ ID NO 32
<211> LENGTH: 30
<212> TYPE: DNA
<213> ORGANISM: Artificial Sequence
<220> FEATURE:
<223> OTHER INFORMATION: HBV genome fragment

<400> SEQUENCE: 32
ggagtccgcg taaagagagg tgcgccccgt                                             30

<210> SEQ ID NO 33
<211> LENGTH: 33
<212> TYPE: DNA
<213> ORGANISM: Artificial Sequence
<220> FEATURE:
<223> OTHER INFORMATION: HBV genome fragment

<400> SEQUENCE: 33
```
cgagggagtt cttcttctag gggacctgcc tcg                33

<210> SEQ ID NO 34
<211> LENGTH: 33
<212> TYPE: DNA
<213> ORGANISM: Artificial Sequence
<220> FEATURE:
<223> OTHER INFORMATION: HBV genome fragment

<400> SEQUENCE: 34
gtcccctaga agaagaactc cctcgcctcg cag                33

<210> SEQ ID NO 35
<211> LENGTH: 30
<212> TYPE: DNA
<213> ORGANISM: Artificial Sequence
<220> FEATURE:
<223> OTHER INFORMATION: Maize ADH gene fragment

<400> SEQUENCE: 35
ccaagcggtg gcggcggagg acggcactgc                30

<210> SEQ ID NO 36
<211> LENGTH: 30
<212> TYPE: DNA
<213> ORGANISM: Artificial Sequence
<220> FEATURE:
<223> OTHER INFORMATION: Maize ADH gene fragment

<400> SEQUENCE: 36
gtcctccgcc gccaccgctt ggcgattgtc                30

<210> SEQ ID NO 37
<211> LENGTH: 33
<212> TYPE: DNA
<213> ORGANISM: Artificial Sequence
<220> FEATURE:
<223> OTHER INFORMATION: HIV genome fragment

<400> SEQUENCE: 37
atagtggcca gctgtgataa atgtcagcta aaa                33

<210> SEQ ID NO 38
<211> LENGTH: 33
<212> TYPE: DNA
<213> ORGANISM: Artificial Sequence
<220> FEATURE:
<223> OTHER INFORMATION: HIV genome fragment

<400> SEQUENCE: 38
gacatttatc acagctggct actatttctt ttt                33

<210> SEQ ID NO 39
<211> LENGTH: 41
<212> TYPE: DNA
<213> ORGANISM: Artificial Sequence
<220> FEATURE:
<223> OTHER INFORMATION: HIV genome fragment

<400> SEQUENCE: 39
agtctacctg accatgaatt gcttcccctt ttatatggca t                41

<210> SEQ ID NO 40
<211> LENGTH: 41
<212> TYPE: DNA

```
<213> ORGANISM: Artificial Sequence
<220> FEATURE:
<223> OTHER INFORMATION: HIV genome fragment

<400> SEQUENCE: 40
taaaagggga agcaattcat ggtcaggtag actacagtcc a                    41

<210> SEQ ID NO 41
<211> LENGTH: 4
<212> TYPE: DNA
<213> ORGANISM: Artificial Sequence
<220> FEATURE:
<223> OTHER INFORMATION: HBV detection probe fragment

<400> SEQUENCE: 41 tttt                                                             4

<210> SEQ ID NO 42
<211> LENGTH: 18
<212> TYPE: DNA
<213> ORGANISM: Artificial Sequence
<220> FEATURE:
<223> OTHER INFORMATION: HBV detection probe fragment

<400> SEQUENCE: 42
ggagttcttc ttctaggg                                              18

<210> SEQ ID NO 43
<211> LENGTH: 4
<212> TYPE: DNA
<213> ORGANISM: Artificial Sequence
<220> FEATURE:
<223> OTHER INFORMATION: HBV detection probe fragment

<400> SEQUENCE: 43 gacc                                                             4

<210> SEQ ID NO 44
<211> LENGTH: 18
<212> TYPE: DNA
<213> ORGANISM: Artificial Sequence
<220> FEATURE:
<223> OTHER INFORMATION: HBV detection probe fragment

<400> SEQUENCE: 44
ccctagaaga agaactcc                                              18

<210> SEQ ID NO 45
<211> LENGTH: 4
<212> TYPE: DNA
<213> ORGANISM: Artificial Sequence
<220> FEATURE:
<223> OTHER INFORMATION: HBV detection probe fragment

<400> SEQUENCE: 45 ctcg                                                             4

<210> SEQ ID NO 46
<211> LENGTH: 6
<212> TYPE: DNA
<213> ORGANISM: Artificial Sequence
<220> FEATURE:
<223> OTHER INFORMATION: HBV detection probe fragment

<400> SEQUENCE: 46 tttttt                                                           6
```

<210> SEQ ID NO 47
<211> LENGTH: 14
<212> TYPE: DNA
<213> ORGANISM: Artificial Sequence
<220> FEATURE:
<223> OTHER INFORMATION: HBV detection probe fragment

<400> SEQUENCE: 47
gggagttctt cttc                                                         14

<210> SEQ ID NO 48
<211> LENGTH: 6
<212> TYPE: DNA
<213> ORGANISM: Artificial Sequence
<220> FEATURE:
<223> OTHER INFORMATION: HBV detection probe fragment

<400> SEQUENCE: 48 tagggg                                                                   6

<210> SEQ ID NO 49
<211> LENGTH: 14
<212> TYPE: DNA
<213> ORGANISM: Artificial Sequence
<220> FEATURE:
<223> OTHER INFORMATION: HBV detection probe fragment

<400> SEQUENCE: 49
gaagaagaac tccc                                                         14

<210> SEQ ID NO 50
<211> LENGTH: 6
<212> TYPE: DNA
<213> ORGANISM: Artificial Sequence
<220> FEATURE:
<223> OTHER INFORMATION: HBV detection probe fragment

<400> SEQUENCE: 50 tcgcct                                                                   6

<210> SEQ ID NO 51
<211> LENGTH: 14
<212> TYPE: DNA
<213> ORGANISM: Artificial Sequence
<220> FEATURE:
<223> OTHER INFORMATION: HBV detection probe fragment

<400> SEQUENCE: 51
ctctttacgc ggac                                                         14

<210> SEQ ID NO 52
<211> LENGTH: 6
<212> TYPE: DNA
<213> ORGANISM: Artificial Sequence
<220> FEATURE:
<223> OTHER INFORMATION: HBV detection probe fragment

<400> SEQUENCE: 52 tccccg                                                                   6

<210> SEQ ID NO 53
<211> LENGTH: 14
<212> TYPE: DNA
<213> ORGANISM: Artificial Sequence
<220> FEATURE:

```
<223> OTHER INFORMATION: HBV detection probe fragment

<400> SEQUENCE: 53
gtccgcgtaa agag                                                    14

<210> SEQ ID NO 54
<211> LENGTH: 6
<212> TYPE: DNA
<213> ORGANISM: Artificial Sequence
<220> FEATURE:
<223> OTHER INFORMATION: HBV detection probe fragment

<400> SEQUENCE: 54 aggtgc                                                              6

<210> SEQ ID NO 55
<211> LENGTH: 16
<212> TYPE: DNA
<213> ORGANISM: Artificial Sequence
<220> FEATURE:
<223> OTHER INFORMATION: HIV detection probe fragment

<400> SEQUENCE: 55
ccagctgtga taaatg                                                  16

<210> SEQ ID NO 56
<211> LENGTH: 4
<212> TYPE: DNA
<213> ORGANISM: Artificial Sequence
<220> FEATURE:
<223> OTHER INFORMATION: HIV detection probe fragment

<400> SEQUENCE: 56 tcag                                                                4

<210> SEQ ID NO 57
<211> LENGTH: 16
<212> TYPE: DNA
<213> ORGANISM: Artificial Sequence
<220> FEATURE:
<223> OTHER INFORMATION: HIV detection probe fragment

<400> SEQUENCE: 57
catttatcac agctgg                                                  16

<210> SEQ ID NO 58
<211> LENGTH: 4
<212> TYPE: DNA
<213> ORGANISM: Artificial Sequence
<220> FEATURE:
<223> OTHER INFORMATION: HIV detection probe fragment

<400> SEQUENCE: 58 ctac                                                                4

<210> SEQ ID NO 59
<211> LENGTH: 18
<212> TYPE: DNA
<213> ORGANISM: Artificial Sequence
<220> FEATURE:
<223> OTHER INFORMATION: HIV detection probe fragment

<400> SEQUENCE: 59
ctgaccatga attgcttc                                                18
```

```
<210> SEQ ID NO 60
<211> LENGTH: 4
<212> TYPE: DNA
<213> ORGANISM: Artificial Sequence
<220> FEATURE:
<223> OTHER INFORMATION: HIV detection probe fragment

<400> SEQUENCE: 60 ccct                                                                  4

<210> SEQ ID NO 61
<211> LENGTH: 18
<212> TYPE: DNA
<213> ORGANISM: Artificial Sequence
<220> FEATURE:
<223> OTHER INFORMATION: HIV detection probe fragment

<400> SEQUENCE: 61
gaagcaattc atggtcag                                                  18

<210> SEQ ID NO 62
<211> LENGTH: 4
<212> TYPE: DNA
<213> ORGANISM: Artificial Sequence
<220> FEATURE:
<223> OTHER INFORMATION: HIV detection probe fragment

<400> SEQUENCE: 62 gtag                                                                  4

<210> SEQ ID NO 63
<211> LENGTH: 14
<212> TYPE: DNA
<213> ORGANISM: Artificial Sequence
<220> FEATURE:
<223> OTHER INFORMATION: Internal control detection probe fragment

<400> SEQUENCE: 63
aagcggtggc ggcg                                                      14

<210> SEQ ID NO 64
<211> LENGTH: 6
<212> TYPE: DNA
<213> ORGANISM: Artificial Sequence
<220> FEATURE:
<223> OTHER INFORMATION: Internal control detection probe fragment

<400> SEQUENCE: 64 gaggac                                                                6

<210> SEQ ID NO 65
<211> LENGTH: 14
<212> TYPE: DNA
<213> ORGANISM: Artificial Sequence
<220> FEATURE:
<223> OTHER INFORMATION: Internal control detection probe fragment

<400> SEQUENCE: 65
cgccgccacc gctt                                                      14

<210> SEQ ID NO 66
<211> LENGTH: 6
<212> TYPE: DNA
<213> ORGANISM: Artificial Sequence
<220> FEATURE:
<223> OTHER INFORMATION: Internal control detection probe fragment
```

```
<400> SEQUENCE: 66 ggcgat                                                                      6

<210> SEQ ID NO 67
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 67
ttttctctct ttacgcggac tccccg                                               26

<210> SEQ ID NO 68
<211> LENGTH: 26
<212> TYPE: DNA
<213> ORGANISM: Artificial Sequence
<220> FEATURE:
<223> OTHER INFORMATION: Probe for the detection of HBV genome

<400> SEQUENCE: 68
ttttgagtcc gcgtaaagag aggtgc                                               26

<210> SEQ ID NO 69
<211> LENGTH: 24
<212> TYPE: DNA
<213> ORGANISM: Artificial Sequence
<220> FEATURE:
<223> OTHER INFORMATION: Probe for the detection of an internal control

<400> SEQUENCE: 69
ttttaagcgg tggcggcgga ggac                                                 24

<210> SEQ ID NO 70
<211> LENGTH: 24
<212> TYPE: DNA
<213> ORGANISM: Artificial Sequence
<220> FEATURE:
<223> OTHER INFORMATION: Probe for the detection of an internal control

<400> SEQUENCE: 70
tttttccgcc gccaccgctt ggcg                                                 24

<210> SEQ ID NO 71
<211> LENGTH: 37
<212> TYPE: DNA
<213> ORGANISM: Artificial Sequence
<220> FEATURE:
<223> OTHER INFORMATION: Probe for the detection of Salmonella

<400> SEQUENCE: 71
cgcgactgtc agaatagtga gcgtgcctta cgtcgcg                                   37

<210> SEQ ID NO 72
<211> LENGTH: 25
<212> TYPE: DNA
<213> ORGANISM: Artificial Sequence
<220> FEATURE:
<223> OTHER INFORMATION: Probe for the detection of Salmonella

<400> SEQUENCE: 72
tttgaatagt gagcgtgcct taccg                                                25

<210> SEQ ID NO 73
<211> LENGTH: 25
```

```
<212> TYPE: DNA
<213> ORGANISM: Artificial Sequence
<220> FEATURE:
<223> OTHER INFORMATION: Probe for the detection of Salmonella

<400> SEQUENCE: 73
tttaggcacg ctcactattc tgaca                                         25

<210> SEQ ID NO 74
<211> LENGTH: 22
<212> TYPE: DNA
<213> ORGANISM: Artificial Sequence
<220> FEATURE:
<223> OTHER INFORMATION: PCR primer

<400> SEQUENCE: 74
cacgcaggaa ataacaggac tt                                            22

<210> SEQ ID NO 75
<211> LENGTH: 17
<212> TYPE: DNA
<213> ORGANISM: Artificial Sequence
<220> FEATURE:
<223> OTHER INFORMATION: PCR primer

<400> SEQUENCE: 75
gggcaaccag cactaac                                                  17

<210> SEQ ID NO 76
<211> LENGTH: 18
<212> TYPE: DNA
<213> ORGANISM: Artificial Sequence
<220> FEATURE:
<223> OTHER INFORMATION: HBV detection probe fragment

<400> SEQUENCE: 76
ctctctttac gcggactc                                                 18

<210> SEQ ID NO 77
<211> LENGTH: 4
<212> TYPE: DNA
<213> ORGANISM: Artificial Sequence
<220> FEATURE:
<223> OTHER INFORMATION: HBV detection probe fragment

<400> SEQUENCE: 77 cccg                                                                 4

<210> SEQ ID NO 78
<211> LENGTH: 18
<212> TYPE: DNA
<213> ORGANISM: Artificial Sequence
<220> FEATURE:
<223> OTHER INFORMATION: HBV detection probe fragment

<400> SEQUENCE: 78
gagtccgcgt aaagagag                                                 18

<210> SEQ ID NO 79
<211> LENGTH: 4
<212> TYPE: DNA
<213> ORGANISM: Artificial Sequence
<220> FEATURE:
<223> OTHER INFORMATION: HBV detection probe fragment

<400> SEQUENCE: 79
``` gtgc                                                                    4

<210> SEQ ID NO 80
<211> LENGTH: 16
<212> TYPE: DNA
<213> ORGANISM: Artificial Sequence
<220> FEATURE:
<223> OTHER INFORMATION: Internal control detection probe fragment

<400> SEQUENCE: 80
aagcggtggc ggcgga                                                       16

<210> SEQ ID NO 81
<211> LENGTH: 4
<212> TYPE: DNA
<213> ORGANISM: Artificial Sequence
<220> FEATURE:
<223> OTHER INFORMATION: Internal control detection probe fragment

<400> SEQUENCE: 81 ggac                                                                    4

<210> SEQ ID NO 82
<211> LENGTH: 16
<212> TYPE: DNA
<213> ORGANISM: Artificial Sequence
<220> FEATURE:
<223> OTHER INFORMATION: Internal control detection probe fragment

<400> SEQUENCE: 82
tccgccgcca ccgctt                                                       16

<210> SEQ ID NO 83
<211> LENGTH: 4
<212> TYPE: DNA
<213> ORGANISM: Artificial Sequence
<220> FEATURE:
<223> OTHER INFORMATION: Internal control detection probe fragment

<400> SEQUENCE: 83 ggcg                                                                    4

<210> SEQ ID NO 84
<211> LENGTH: 41
<212> TYPE: DNA
<213> ORGANISM: Artificial Sequence
<220> FEATURE:
<223> OTHER INFORMATION: Salmonella typhi genome fragment

<400> SEQUENCE: 84
ctgaatattg tcagaatagt gagcgtgcct taccgacgat a                           41

<210> SEQ ID NO 85
<211> LENGTH: 41
<212> TYPE: DNA
<213> ORGANISM: Artificial Sequence
<220> FEATURE:
<223> OTHER INFORMATION: Salmonella typhi genome fragment

<400> SEQUENCE: 85
tatcgtcggt aaggcacgct cactattctg acaatattca g                           41

<210> SEQ ID NO 86
<211> LENGTH: 3
<212> TYPE: DNA
<213> ORGANISM: Artificial Sequence -continued

```
<220> FEATURE:
<223> OTHER INFORMATION: Salmonella detection probe fragment

<400> SEQUENCE: 86 ttt                                                                   3

<210> SEQ ID NO 87
<211> LENGTH: 17
<212> TYPE: DNA
<213> ORGANISM: Artificial Sequence
<220> FEATURE:
<223> OTHER INFORMATION: Salmonella detection probe fragment

<400> SEQUENCE: 87
gaatagtgag cgtgcct                                                   17

<210> SEQ ID NO 88
<211> LENGTH: 5
<212> TYPE: DNA
<213> ORGANISM: Artificial Sequence
<220> FEATURE:
<223> OTHER INFORMATION: Salmonella detection probe fragment

<400> SEQUENCE: 88 taccg                                                                 5

<210> SEQ ID NO 89
<211> LENGTH: 17
<212> TYPE: DNA
<213> ORGANISM: Artificial Sequence
<220> FEATURE:
<223> OTHER INFORMATION: Salmonella detection probe fragment

<400> SEQUENCE: 89
aggcacgctc actattc                                                   17

<210> SEQ ID NO 90
<211> LENGTH: 5
<212> TYPE: DNA
<213> ORGANISM: Artificial Sequence
<220> FEATURE:
<223> OTHER INFORMATION: Salmonella detection probe fragment

<400> SEQUENCE: 90 tgaca                                                                 5

<210> SEQ ID NO 91
<211> LENGTH: 35
<212> TYPE: DNA
<213> ORGANISM: Artificial Sequence
<220> FEATURE:
<223> OTHER INFORMATION: Target nucleic acid

<400> SEQUENCE: 91
ggcaggtccc ctagaagaag aactccctcg cctcg                               35

<210> SEQ ID NO 92
<211> LENGTH: 34
<212> TYPE: DNA
<213> ORGANISM: Artificial Sequence
<220> FEATURE:
<223> OTHER INFORMATION: Target nucleic acid

<400> SEQUENCE: 92
cgaggcgagg gagttcttct tctaggggac ctgc                                34
```

DOUBLE-STRANDED PROBES FOR THE FLUORESCENT DETECTION OF NUCLEIC ACIDS

The present application is the U.S. National Phase of PCT International Patent Application No. PCT/IB2007/003029, filed Oct. 12, 2007, which claims the benefit of European Patent Application No. 06291594.7, filed Oct. 12, 2006, both of which are hereby incorporated by reference in their entireties.

The present invention relates to a double-stranded nucleotide probe intended for the fluorescent detection of nucleic acids.

Nucleic acid quantification is currently of a wide medical use, in particular in the field of virology. Indeed, viral load determination in individuals suffering from chronic viral diseases, such as hepatitis B or AIDS, is now indissociable from the management of these pathologies, notably to monitor the efficacy of drug regimens.

Among the various known methods for nucleic acid quantification, real-time Polymerase Chain Reaction (PCR) is currently the most valued method, given both its sensitivity and its specificity.

Real-time PCR associates nucleic acid amplification and fluorescent detection of the amplified nucleic acids. Briefly, a standard PCR intended for the amplification of a target nucleic acid is carried out in the presence of probes which specifically yield a fluorescence signal when bound to the target nucleic acid, and fluorescence emission is monitored while the PCR cycles proceed. The cycle for which fluorescence emitted from the PCR is measured above a threshold level (i.e. above a background fluorescence level), is called the threshold cycle (Ct). It has been shown that Ct is proportional to the decimal logarithm of the amount of target nucleic acid which is initially present in the PCR (see "Real-time PCR" in Advanced Methods S., Dorak M T. ed, Taylor and Francis, Oxford, 2006). Thus, determination of Ct enables the determination of the initial concentration of a target nucleic acid in a sample.

The success of this method has led to the development of various fluorescent probes intended to yield a minimum amount of fluorescence when unbound to the target nucleic acid and a maximum amount of fluorescence when bound to the target nucleic acid. One way to achieve this objective is to provide probes labelled with fluorescent and quenching moieties in a way such that the latter moieties are in close proximity when the probe is unbound to the target nucleic acid—to prevent fluorescence emission—and sufficiently apart from one another when the probe is bound to the target nucleic acid—to enable fluorescence emission.

Thus, Morisson (U.S. Pat. No. 5,928,862) provides a double-stranded nucleotide probe, wherein the strands are totally complementary to one another and to the strands of the target nucleic acid, each strand of the probe carrying a fluorescent donor e.g. at the 5' end and a fluorescent acceptor e.g. at the 3' end. When the probe is unbound to the target nucleic acid, fluorescence emission is quenched because fluorescent and quenching moieties face each other in the double-stranded probe. In contrast, when the probe is bound to the target nucleic acid, the fluorescent and quenching moieties are separated from each other, thereby allowing fluorescence to be emitted.

However, these probes suffer from a major drawback. Indeed, there is no significant difference in the melting temperatures of the double-stranded probe in itself and of the duplexes between the probe strands and the target nucleic acid strands. Therefore, during the annealing phase of a real-time PCR cycle, there is a competition between probe strands binding to themselves on one hand and probe strands binding to the target nucleic acid on the other hand, which results in a decreased fluorescence emission and, as consequence, a decreased sensitivity of the real-time PCR. Furthermore, the fluorescence emission of the fluorescent donor is partially quenched by the nucleobases at the ends of the double DNA helix formed by the probe bound to the target nucleic acid.

These problems are partially solved in view of the so-called Molecular Beacon probes, which are notably disclosed in the international patent application WO 98/10096.

The Molecular Beacon probes usually take the form of a nucleotide probe folded into a stem-loop structure, wherein one end of the stem is linked to a fluorescent donor while the other end is linked to a fluorescent acceptor. As such, no fluorescence is emitted from the probe when folded into the stem-loop structure, while when unfolded, fluorescence is emitted from the probe. Furthermore, these probes are designed in such a way that the melting temperature of the stem is lower than the melting temperature of the loop sequence with respect to its complementary sequence on the target nucleic acid. As such, there is only a very limited competition between probe binding to itself and probe binding to the target nucleic acid during the annealing phase of the PCR.

The Molecular Beacon probes are relatively long oligonucleotides (between 35 to 45 nucleotides in length). Such large sizes can prove problematic when designing these probes, especially when the targets to be detected are constituted from variable parts of a nucleic acid sequence. Moreover, chemical synthesis of such double-labelled long oligonucleotides is labor-consuming and costly.

In addition, the design of such probes usually proves to be a tedious task, since the balance which is to be found between the stem and the loop melting temperatures is often delicate to achieve. Indeed, this balance notably depends on the fluorescent donor—fluorescent acceptor couple used, on the length and the sequence of the stem, as well as on the length and the sequence of the loop. This problem is reinforced in case of multiplex assays where all probes have to be functional in a short range of PCR annealing temperatures.

Another drawback worth noting concerning these probes lies in the formation of internal secondary structures during hybridization steps, which limits the specific hybridization of the probe to its target. Such a limitation can be critical in multiplex real-time amplification assays.

Other probes, used in the so-called "TaqMan®" hybridization assay (Gelfand et al. U.S. Pat. Nos. 5,210,015, 5,487,972; and Livak at al. U.S. Pat. Nos. 5,538,848, 5,723,591, 6,258, 569) also make use of a fluorescent donor—fluorescent acceptor system. These probes are constituted of a single-stranded oligonucleotide labelled with a fluorescent donor and a fluorescent acceptor located at either ends of the probes thus forming a FRET (Fluorescence Resonance Energy Transfer) pair. A nucleic acid polymerase having a 5' to 3' exonuclease activity is used in the assay which releases single or multiple nucleotides by cleavage of the nucleotide probe when it is hybridized to a target strand. This cleavage separates the fluorescent donor and the fluorescent acceptor, thus disrupting the FRET pair and enabling fluorescence emission.

These probes suffer from two major drawbacks. Firstly, the TaqMan® method requires the use of specific Taq polymerase enzymes having a 5' to 3' exonuclease activity. Secondly, the synthesis of the oligonucleotides carrying two different labels at specific locations and a blocking group on the 3' terminal nucleotide to prevent extension by the nucleic acid polymerase results in a number of subproducts. The presence of these subproducts requires labor-intensive purification, which results in higher cost.

As such, it is an object of the present invention to provide fluorescent probes, combining the use of fluorescent donors and acceptors devoid of the drawbacks associated with the probes already known in the art.

The present Inventors have solved the above problems by providing the following double-stranded probes, which are exemplified in FIGS. 1 and 2.

The probes according to the invention are constituted of two strands partially complementary to one another. The binding of these strands to respective target nucleic acid strands is favoured over their mutual binding, this being achieved by providing, on each strand of the double-stranded probe, a nucleotide sequence designed to bind to the target nucleic acid but not to the other strand of the probe. The melting temperature of such double-stranded probe is lower than the melting temperature of the complex formed from the first and second strand of the double stranded-probe with respectively the first and second strand of the target nucleic acid.

Such double-stranded probes can be easily adapted to match for any particular target nucleic acid.

Furthermore, the probes according to the invention provide in general for an increased fluorescence with respect to the other fluorescent probes known in the art when tested in optimal PCR conditions, by providing a spacer moiety between the fluorescent donor and the rest of the probe, thereby preventing quenching which may result from the proximity of the nucleobases at the ends of the double-helix which is formed between the strands of the probe and the target nucleic acid.

The inventors have also evidenced that unexpectedly double-stranded probes according to the invention are not strictly dependent of a specific annealing temperature, thus providing a real advantage in multiplex assays.

Thus, the present invention relates to a double-stranded probe intended for the fluorescent detection of a single-stranded or double-stranded target nucleic acid, comprising:

a first strand of formula $X_1$-$(L_1)_a$-$S_1$-$S'_1$-$(L'_1)_b$-$Y_1$, intended for the detection of a first strand of the target nucleic acid which comprises a sequence of formula $T'_1$-$T_1$;

a second strand of formula $X_2$-$(L_2)_c$-$S_2$-$S'_2$-$(L'_2)_d$-$Y_2$, intended for the detection of a second strand of the target nucleic acid, if present, said second strand of the target nucleic acid comprising a sequence of formula $T'_2$-$T_2$;

wherein:

two of $X_1$, $X_2$, $Y_1$, and $Y_2$ represent a fluorescent donor, while the two others represent a fluorescent acceptor, and $X_1$ and $Y_2$ cannot both represent a fluorescent donor;

a, b, c, and d represent 0 or 1, provided that a, b, c, or d represent 1 when respectively $X_1$, $X_2$, $Y_1$, or $Y_2$ represent a fluorescent donor;

$T_1$ and $T_2$ represent oligonucleotide sequences having from 10 to 35 nucleotides, more preferably from 12 to 20 nucleotides, which are complementary to one another;

independently from one another, $T'_1$ and $T'_2$ represent oligonucleotide sequences having from 2 to 8 nucleotides;

$S_1$ and $S_2$ represent oligonucleotide sequences having from 10 to 35 nucleotides, more preferably from 12 to 20, nucleotides which are complementary to one another, $S_1$ being at least 85% complementary to $T_1$, and $S_2$ being at least 85% complementary to $T_2$;

independently from one another, $S'_1$ and $S'_2$, represent oligonucleotide sequences having from 2 to 8 nucleotides, $S'_1$ being at least 65% complementary to $T'_1$, and $S'_2$ being at least 65% complementary to $T'_2$;

$L_1$ and $L_2$ are spacer moieties such that the respective gyration radius of $X_1$ and $X_2$ with respect to the attachment sites of $S_1$ to $L_1$ and $S_2$ to $L_2$ is of at least 3.4 Å;

$L'_1$ and $L'_2$ are spacer moieties such that the respective gyration radius of $Y_1$ and $Y_2$ with respect to the attachment sites of $S'_1$ to $L'_1$ and $S'_2$ to $L'_2$ is of at least 3.4 Å;

the melting temperature of the double-stranded probe being lower than the melting temperature of the complex formed between the first strand of the double stranded-probe and the first strand of the target nucleic acid; and lower than the melting temperature of the complex formed between the second strand of the double stranded-probe and the second strand of the target nucleic acid, if present.

As intended herein, unless when stated otherwise, the polynucleotides which are comprised in the strands, the sequences or the moieties, represented by the following formulae: $X_1$-$(L_1)_a$-$S_1$-$S'_1$-$(L'_1)_b$-$Y_1$, $X_2$-$(L_2)_c$-$S_2$-$S'_2$-$(L'_2)_d$-$Y_2$, $T_1$-$T_1$, $T'_2$-$T_2$, $S_1$-$S'_1$, $S_2$-$S'_2$, $S_1$, $S'_1$, $S_2$, $S'_2$, $L_1$, $L'_1$, $L_2$, $L'_2$ can be in the 5' to 3' or 3' to 5' orientation. However, as will be apparent to the man skilled in the art, within a same formula all the polynucleotides have the same orientation. Besides, for a given double-stranded probe, all formulae are meant to be read in the same orientation, e.g. the polynucleotides which are comprised in the strands represented by $X_1$-$(L_1)_a$-$S_1$-$S'_1$-$(L'_1)_b$-$Y_1$ and $X_2$-$(L_2)_c$-$S_2$-$S'_2$-$(L'_2)_d$-$Y_2$ are either all in the 5' to 3' orientation are all in the 3' to 5' orientation.

As intended herein, "nucleotide" encompasses all known natural and non-natural nucleotides, particularly natural and non-natural ribonucleotides and deoxyribonucleotides.

Preferred non-natural nucleotides to be used within the frame of the invention can be selected from the group constituted of synthetic nucleotides having modified base moieties and/or modified sugar moieties that are capable of specific hybridization (designed to enhance binding property, reduce degeneracy, increase specificity and the like), for example: C-5 Methyl pyrimidine nucleosides, 2,6-diaminopurine 2'-deoxyriboside, G-Clamp (phenoxazine analog), N-4-Ethyl 2'-deoxyCytidine, 2'-deoxyinosine, 2'-deoxynébularine and 3-nitropyrrole 2' deoxynucleoside.

As intended herein, the expression "oligonucleotide" relates to polynucleotides having from 2 to 100 nucleotides, with or without modified backbone and/or modified linkage between nucleotides. Polynucleotides having modified backbone and/or modified linkage between nucleotides notably encompass LNA (Locked Nucleic Acids), PNA (peptide Nucleic Acids) and the like. Analogs of phosphodiester linkages notably include phosphorothioate, phosphorodithioate, phosphoramidate and the like.

As intended herein, "nucleic acid target" relates to any naturally occurring or synthetic polymer of nucleotides as defined above, such as single or double stranded deoxyribonucleic acid (hereinafter "DNA"), ribonucleic acid (hereinafter "RNA"). In particular the target nucleic acids originate or derive from rRNA, mRNA, plasmidic DNA, bacterial DNA, viral DNA, viral RNA, and chromosomal DNA.

As intended herein a "fluorescent donor" relates to a fluorophor, i.e. a molecule which, upon absorbing energy of a specific wavelength (excitation wavelength), re-emits energy through a signal of fluorescence at a specific longer wavelength (emission wavelength). Fluorophors are well known to the man skilled in the art and are notably described in European patent application EP 1 173 519; in PCT publication WO 2004/055117; by Drexhage K. H. "Structure and properties of laser dyes" in *Dye Lasers, Third Edition*, F. P. Schafer, Ed., Springer-Verlag, (1990) pp. 155-200; by Valeur B. "Molecular Fluorescence: Principles and Applications", Ed. WILEY-VCH Verlag GmbH, 2001; Berlman, I. B., Handbook of Fluorescence Spectra of Aromatic Molecules", Second Edition, Academic Press (1971); Griffiths J. "Colour and Constitution of Organic Molecules", Academic Press (1976).

As intended herein a "fluorescent acceptor" relates to a molecule which absorbs the energy emitted from an associated fluorophor, with or without subsequent emission of a fluorescence photon at another wavelength. If subsequent energy emission occurs the fluorescent acceptor is itself a fluorophor. If no subsequent energy emission occurs the fluorescent acceptor is a quencher. Fluorescent acceptors are well known to the man skilled in the art and are notably described in Chen et al. (1998) *Science* 279:851-3; by Haugland R P. In "Handbook of Fluorescent probes and Research Chemicals", 1992-1994; in PCT publication WO 01/86001; by Lukhtanov et al. (2001) *American Biotechnology Laboratory* 19:68-69; and by Clegg et al. (1992) *Methods in Enzymology* 211:353-389.

As is intended herein when the two strands of the double-stranded probe are hybridized to one another, the fluorescent donors are positioned in close proximity to the fluorescence acceptors. This results in minimal fluorescence emission at the emission wavelength of the fluorescent donor to be emitted from the double stranded probe. In case the fluorescent acceptor is a quencher, then minimal fluorescence is emitted whichever the wavelength. This effect is removed when either strand of the double-stranded probe is bound to its respective cognate target, due to the distance separating the fluorescence donor from the fluorescence acceptor.

There is a great deal of practical guidance in the literature for selecting appropriate donor/acceptor pairs, e.g. Wu et al. (1994) *Anal. Biochem.* 218:1-13; White et al. "Fluorescence Analysis: A Practical Approach" Marcel Dekker, New York, 1970.

Many suitable forms of the fluorescent donors and acceptors are commercially available with substituents as the bonding functionality for attachment to an oligonucleotide.

Preferably, fluorescent donors and acceptors derivatized with a phosphoramidite moiety are employed because they are attached directly to the 5'OH of the oligonucleotide at the conclusion of the solid phase synthesis. Thus, the synthesis can be entirely automated, as described e.g. by Mullah et al. (1999) *Nucleosides & Nucleotides* 18:1311-1312. As such, fluorescein dyes and derivatives can be conveniently introduced at the 5' end of an oligonucleotide by using this phosphoramidite chemistry, as described e.g. in U.S. Pat. Nos. 5,583,236, 5,721,355, and EP 0 652 167. A fluorescent donor or acceptor-labelled nucleotide can also be used and incorporated in any part of the oligonucleotide sequence during its synthesis as described by Yang et al. (1997) *Methods in Enzymology* 28:417-441.

Alternative methods for attachment of fluorescent donor or acceptor, called post-synthetic or manual coupling, are also well described e.g. in the following references: Sproat et al. (1987) *Nucleic Acids Research* 15:4837-4848; Sproat et al. (1987) *Nucleic Acids Research* 15: 6181-6196; Markiewicz et al. (1989) *Nucleic Acids Research* 17:7149-7158; Agrawal "Protocols in Oligonucleotide Conjugates" in *Methods in Molecular Biology*, Humana Press, Totowa, N.J., 1994.

5' end modified oligonucleotides can be synthesized by direct incorporation of a 5' amino group or a 5' sulfhydryl group for instance by using a 5'-Thiol Modifier C6 and 5'-Amino Modifier C6 (e.g. from Glen Research). A halogenoacetamide or maleimide derivative of the fluorescent acceptor or donor is coupled to the sulfhydryl group or a succinimidyl derivative of the fluorescent acceptor or donor is coupled to the amino group. This chemistry is very useful for sensitive fluorescent donors or acceptors which are not stable during the automated synthesis and/or damaged by the treatment needed for the deprotection and cleavage from the solid support (generally, concentrated ammoniac), like the tetramethylrhodamine (TAMRA), the cyanine dyes or others.

To introduce a label at the 3' end of an oligonucleotide, modified columns (i.e. controlled-pored glass or polystyrene) can be used, preferably directly on the automated synthesizer. The amino, group of the support is covalently linked to the label. Quenchers can particularly be introduced by this way.

Another well-known methodology to introduce a label at the 3' end of an oligonucleotide is to functionalize the 3' end of the oligonucleotide with an amino group and to use a succinimidyl derivative of the fluorescent donor or acceptor, as described e.g. by Nelson et al. (1989) *Nucleic Acids Research* 17:7187-7194.

As intended herein the expression "spacer moiety" relates to any chemical group which is liable to be bound to a nucleic acid. This spacer moiety is useful to prevent quenching of the fluorescence emitted from a fluorescent donor which might result from the proximity of the nucleobases at the ends of the double-helix which is formed between the strands of the probe and the target nucleic acid.

As intended herein the expression "gyration radius" relates to the distance between $S_1$ or $S_2$ attachment site on the spacer moieties $L_1$ and $L_2$ and respectively $X_1$ or $X_2$ attachment site on the same moieties, in the spacer moieties most extended conformation, or to the distance between $S'_1$ or $S'_2$ attachment site on the spacer moieties $L'_1$ and $L'_2$ and respectively $Y_1$ or $Y_2$ attachment site on the same moieties, in the spacer moieties most extended conformation. It should also be noted that as intended in the invention, $X_1$ and $X_2$ can be respectively linked to any part of $L_1$ and $L_2$, and $Y_1$ and $Y_2$ can be respectively linked to any part of and $L'_1$ and $L_2$, e.g. alongside or at extremities, as long as the condition on the gyration radius is observed.

A distance of at least 3.4 Å is found necessary to ensure that minimum quenching of the fluorescent donor occurs because of the proximity of the nucleobases constituting $S_1$ or $S_2$. Indeed, nucleotides, in particular G nucleotides, are well-known to have quenching properties.

By way of example, the quenching efficiencies (%) of natural nucleotides vis-a-vis particular fluorophors are set out in the following table:

| Fluorophor | Adenosine | Cytidine | Guanosine | Thymidine |
| --- | --- | --- | --- | --- |
| Fluorescein (FAM) | 23 | 8 | 32 | 8 |
| Tetrachlorofluorescein (TET) | 16 | 16 | 35 | 14 |
| Hexachlorofluorescein (HEX) | 62 | 56 | 69 | 65 |
| Tetramethylfluorescein (TAMRA) | 9 | 11 | 20 | 11 |
| Texas Red ® | 22 | 11 | 8 | 11 |
| Cyanine 5 (Cy5) | 15 | 15 | 19 | 10 |

The spacer moiety ($L_1$, $L_2$, $L_1'$, or $L_2'$) may comprise a specific linker moiety for coupling with a fluorescent donor or acceptor. This can be for instance a hydroxyl function protected by a dimethoxytrityl group or any other acid-labile protective group, preferably compatible with automated synthesizer chemistry.

As intended herein, the expression "complementary" denotes two nucleotide sequences of the same length which bases fully match.

As intended herein, the expression "X % complementarity" means that two sequences of the same length which are aligned pairwise on their whole length comprise X % of bases which are matching.

As intended herein, the expression "melting temperature" (Tm) relates to the temperature point in a hybridization reaction at which half of the nucleotides are denatured (single strands) and half are annealed or hybridized (double strands). The melting temperature is dependent on a set of conditions referred to stringency, e.g. the hybridization buffer used. It can be determined according to methods well-known to the man skilled in the art, such as those described by Wallace et al. (1979) *Nucleic Acid Res.* 6:3543-3558; Breslauer et al. (1986) *Proc. Natl. Acad. Sci. USA* 83:376-3750; and Xia et al. (1998) *Biochemisty*, 37:14719-14735.

The Tm values can be predicted using nearest-neighbor thermodynamic parameters and specific salt corrections, as described e.g. by Breslauer et al. (1986) *Proc. Natl. Acad. Sci. USA* 83:376-3750 and Owczarzy et al. (2004) *Biochemistry* 43:3537-3554. Such predictions are considered accurate for oligonucleotides from 8 to 60 bases in length, in neutral buffered solutions (pH 7-8) with monovalent cation concentrations from 10 mM to 1.2 M. Oligonucleotide concentration is assumed to be significantly larger than concentration of the complementary target. Effects of chemical modifications are neglected. The effects of divalent cations are not accounted. The average error on the Tm thus determined is usually of +/−2° C.

Advantageously, thanks to the spacer moiety, the double-stranded probes according to the invention provide in general for an increased fluorescence with respect to other fluorescent probes known in the art, when tested in optimal PCR conditions. In addition, lower quantities of the double-stranded probes according to the invention can be used in comparison to the prior art fluorescent probes, therefore reducing the cost of assays making use of them and the problems linked to steric hindrance in assays, in particular multiplex assays. Furthermore, the double-stranded probes according to the invention provide for a robust, reproducible and sensitive system, which notably enables the detection of very low quantities of nucleic acids (e.g. 5-10 copies per PCR assay).

Equally advantageous, and unexpectedly, the double-stranded probes according to the invention are not strictly dependent on a specific annealing temperature. This is particularly advantageous when implementing multiplex assays, wherein the various probes which are used have to be functional at the same annealing temperature, by enabling an easier design of the probes and a more important choice in the sequences liable to be used for binding to the target nucleic acids.

Double-stranded probes according to the invention are useful for detecting a target nucleic acid in a sample. Such a target nucleic acid can derive from a micro organism like a virus (e.g. hepatitis C virus (HCV), hepatitis B virus (HBV), Human deficiency virus (HIV), Human Papilloma virus (HPV)), or a bacteria (e.g. *Listeria, Salmonella, Mycobacteria*). The double stranded-probes of the invention are also useful for detecting single nucleotide polymorphism, or insertions, deletions and multiple mutations in nucleic acids, for instance in the frame of the diagnosis or the prognosis of genetic diseases or cancers.

In a preferred embodiment of the above-defined double-stranded probe, b=d=0 (a and c then representing 1) and $X_1$ and $X_2$ represent fluorescent donors, said double-stranded probe being then constituted of:

a first nucleic acid strand of formula $X_1$-$L_1$-$S_1$-$S'_1$-$Y_1$, and
a second nucleic acid strand of formula $X_2$-$L_2$-$S_2$-$S'_2$-$Y_2$.

In another preferred embodiment of the above-defined double-stranded probe, wherein the fluorescent donor is selected from the group consisting of xanthene dyes, rhodamine dyes, carbopyronine dyes and carboxamide dyes.

In another preferred embodiment of the above-defined double-stranded probe, the fluorescent acceptor is selected from the group consisting of Dabcyl (4-(4-dimethylaminophenyl)diazenyl benzoic acid), Dabsyl (4-N,N-dimethylaminoazobenzene-4'sulfonic acid, Black Hole Quencher 1® (BHQ®-1), Black Hole Quencher 2® (BHQ®-2), Black Hole Quencher 3® (BHQ®-3), Iowa Black® (Integrated DNA Technologies, Coralville, IA), Eclipse® (4-N-methyl-N-(4'nitro-2'-chloroazobenzen-4-yl)-aminobutanamido-1-(2-O-dimethoxytrityloxymethyl)-pyrrolidin-4-yl-succinoyl long chain alkylamino-CPG; Epoch Biosciences, Inc.,Bothell, WA), QSY® 7(Xanthylium, 9-[2-[[4-[[(2,5-dioxo-1-pyrrolidinyl)oxy]carbonyl]-1-piperidinyl]sulfonyl]phenyl]-3,6-bis(methylphenylamino)-, chloride), QSY® 9 (N-(9-{2-[(4-{[(2,5-dioxopyrrolidin-1-yl)oxy]carbonyl}piperidin-1-yl)sulfonyl]phenyl}-6-[methyl(4-sulfophenyl)amino]-3H-xanthen-3-ylidene)-N-methyl-4-sulfoanilinium), QSY® 21 (2-[6-(1,3-dihydro-2H-isoindol-2-yl)-9-{2-[(4-{[(2,5-dioxopyrrolidin-1-yl)oxy]carbonyl}piperidin-1-yl)sulfonyl]phenyl}-3H -xanthen-3-ylidene]-2,3-dihudro-1H-isoindolium chloride), DABMI (4-dimethylaminophenylazophenyl-4'-maleimid), Malachite green (4-[(4-dimethylaminophenyl) phenyl-methyl]-N,N-dimethylaniline), coumarin (2H-chromen-2-one), and dark quenchers.

The characteristics of fluorescent donors and acceptors liable to be used in the frame of the invention are presented in the following table:

| Short name | Complete name | Reference | Supplier |
|---|---|---|---|
| FAM | Fluorescein | U.S. Pat. No. 5,585,236 | Pharmacia |
| | | U.S. Pat. No. 5,721,355 | Biotech |
| TET | tetrachlorofluorescein | EP 0652167 | Perkin Elmer |
| HEX | tetrahexafluorescein | EP 0658167 | Perkin Elmer |
| TAMRA | Tetramethylrhodamine | U.S. Pat. No. 4,997,928 | Dupont de |
| | | EP 0359225 | Nemours |
| Cy5 | Cyanine 5 | U.S. Pat. No. 5,556,959 | Pharmacia |
| | | U.S. Pat. No. 5,808,044 | Biotech |
| Texas Red ® | / | U.S. Pat. No. 5,955,612 | Systemix |
| CFO | Cal Fluor Orange | US 2005/0170363 | Biosearch Technologies |
| Quasar 570 | / | US 2005/0214833 | Biosearch Technologies |
| CFRed 590 | Cal Fluor Red 590 | US 2005/0170363 | Biosearch Technologies |

-continued

| Short name | Complete name | Reference | Supplier |
|---|---|---|---|
| CFRed 610 | Cal Fluor Red 610 | US 2005/0170363 | Biosearch Technologies |
| Quasar 670 | / | US 2005/0214833 | Biosearch Technologies |
| Atto532, NK141, NK230 | / | EP 1576059 | Atto-TEC |
| Atto647N | / | EP 1576059 EP 1173519 | Atto-TEC |
| Atto590 | / | / | Atto-TEC |
| Eclipse ® | / | WO 02/099141 WO 01/42505 U.S. Pat. No. 6,790,945 | Epoch Biosciences |
| BHQ ®s | Black Hole Quenchers ® | WO 01/86001 U.S. Pat. No. 7,019,129 | Biosearch Technologies |
| QSY ®s | / | U.S. Pat. No. 6,329,205 | Molecular Probes |
| Iowa Black ® | / | / | Integrated DNA Technologies |
| Dabcyl | 4-((4-Dimethylamino)phenyl)azo Benzoic acid | / | / |

The absorbance (Abs) characteristics of some fluorescent acceptors are presented in the following table:

| Fluorescent acceptor | Abs (nm) | Max Abs (nm) |
|---|---|---|
| Dabcyl | 400-550 | 479 |
| BHQ ®-1 | 480-580 | 534 |
| BHQ ®-2 | 559-650 | 579 |
| BHQ ®-3 | 620-730 | 680 |
| Iowa Black ® | 420-620 | 531 |
| Eclipse ® | 390-625 | 522 |
| QSY ®-7/9 | 500-650 | 560/562 |
| QSY ®-21 | 550-750 | 661 |
| Malachite Green | 550-700 | 628 |

Examples of suitable fluorescent donor/acceptor pairs, including the maximum excitation (Exc) and the maximum emission (Em), which can be used in the context of the invention are reported in the following table:

| Fluorescent donor | Exc/Em (nm) | Fluorescent acceptor |
|---|---|---|
| FAM | 494/530 | Dabcyl, BHQ1, QSY-7/9, Eclipse |
| TET | 512/536 | Dabcyl, BHQ1, QSY-7/9, Eclipse |
| HEX, CFO, Atto532 | 535/556, 540/561, 532/553 | Dabcyl, BHQ1, QSY-7/9, Eclipse |
| Cy3, Quasar570, Atto550 | 552/570, 550/570, 554/576 | Dabcyl, BHQ1, BHQ2, QSY-7/9 |
| TAMRA, CFRed590, Atto565 | 565/580, 565/588, 563/592 | Dabcyl, BHQ2, QSY-7/9 |
| ROX | 585/605 | BHQ2, QSY-21 |
| Texas Red, CFRed610, Atto590 | 595/615, 590/610, 594/624 | Iowa Black FQ, BHQ2, QSY-21 |
| Cy5, Quasar670, Atto647 | 643/667, 649/670, 645/669 | Iowa Black FQ, BHQ3, QSY-21 |

In another preferred embodiment of the above-defined double-stranded probe, $L_1$ and $L_2$ respectively quench less than 25% of the fluorescence of $X_1$ and $X_2$, when $X_1$ and $X_2$ represent fluorescent moieties, and $L'_1$ and $L'_2$ respectively quench less than 25% of the fluorescence of $Y_1$ and $Y_2$, when $Y_1$ and $Y_2$ represent fluorescent moieties.

In another preferred embodiment of the above-defined double-stranded probe, $L_1$, $L_2$, $L'_1$ and/or $L'_2$ comprise at least one positive charge. The presence of at least one positive charge in the spacer moiety ensures that when both strands of the double-stranded probe are associated together the fluorescent and quenching moieties are in close proximity to each other, thanks to electrostatic interactions which occur between the positive charge and the negatively charged phosphate backbones of the DNA strands.

In another preferred embodiment of the above-defined double-stranded probe, $L_1$, $L_2$, $L'_1$ and $L'_2$, identical or different, are selected from the group consisting of a polynucleotide having from 2 to 10 nucleotides, an alkyl or aminoalkyl group having from 3 to 12 carbon atoms, and a polyethylene glycol group having a degree of polymerisation from 2 to 6.

In a further embodiment of the above-defined double-stranded probe, $L_1$, $L_2$, $L'_1$ and $L'_2$, identical or different, represent a polyT polynucleotide. Advantageously, polyT polynucleotides provide for minimum quenching with respect to other polynucleotides.

In another preferred embodiment of the above-defined double-stranded probe, when $L_1$ and/or $L_2$ represents a polynucleotide, then the length of $L_1$ and/or $L_2$ is shorter than that of $S'_2$ and/or $S'_1$ respectively. Advantageously, in such a configuration a fluorescent donor bound to the spacer moiety would be at close proximity to the nucleotides of $S'_2$ and/or $S'_1$ when the strands of the double-stranded probes according to the invention are bound together, thereby being possibly quenched, in particular if $S'_2$ and/or $S'_1$ comprise G nucleotides.

In another preferred embodiment of the above-defined double-stranded probe, when $L_1$ and/or $L_2$ represents a polynucleotide, then $L_1$ and/or $L_2$ presents less than 35% complementarity with $S'_2$ and/or $S'_1$ respectively. Such a low percentage of complementarity is advantageous since it allows the strands of the double-stranded probe according to the invention to particularly preferentially bind to their respective target nucleic acid strand as compared to their mutual binding.

In yet another preferred embodiment of the above-defined double-stranded probe, the melting temperature of the first strand of the probe with respect to the second strand of the probe is at least 10% lower than the melting temperature of either of the probes with respect to their respective target nucleic acid strands. Such a melting temperature is preferred since it allows for a particularly preferential binding of the strands of the double-stranded probe according to the invention to their respective target nucleic acid strand as compared to their mutual binding.

In a preferred embodiment of the above-defined double-stranded probe:
$X_1$ and $X_2$ are selected from the group constituted of FAM, Atto532, NK141, NK230 and Atto647N;
$Y_1$ and $Y_2$ represent Dabcyl;
$L_1$ and $L_2$ represent a polyT polynucleotide having from 3 to 6 nucleotides;
$S_1$ and $S_2$ represent an oligonucleotide sequence having from 14 to 18 nucleotides;
$S'_1$ and $S'_2$ represent an oligonucleotide sequence having from 4 to 6 nucleotides.

In another preferred embodiment of the above-defined double-stranded probe, $S_1$-$S'_1$ represents a fragment of a sequence selected from the group constituted of:
5'-CACCTCTCTTTACGCGGACTCCCCGTCTGT-3' (SEQ ID NO: 31);
$S_2$-$S'_2$ then representing a fragment of 5'-GGAGTCCGCGTAAAGAGAGGTGCGCCCCGT-3' (SEQ ID NO: 32) (such a double-stranded probe being particularly intended for the detection of HBV A Zone);
5'-CGAGGGAGTTCTTCTTCTAGGGGACCTGCCTCG-3' (SEQ ID NO: 33);
$S_2$-$S'_2$ then representing a fragment of 5'-GTCCCCTAGAAGAAGAACTCCCTCGCCTCGCAG-3' (SEQ ID NO: 34) (such a double-stranded probe being particularly intended for the detection of HBV B Zone);
5'-CCAAGCGGTGGCGGCGGAGGACGGCACTGC-3' (SEQ ID NO: 35);
$S_2$-$S'_2$ then representing a fragment of 5'-GTCCTCCGCCGCCACCGCTTGGCGATTGTC-3' (SEQ ID NO: 36) (such a double-stranded probe being particularly intended for the detection of an internal control);
5'-ATAGTGGCCAGCTGTGATAAATGTCAGCTAAAA-3' (SEQ ID NO: 37);
$S_2$-$S'_2$ then representing a fragment of 5'-GACATTTATCACAGCTGGCTACTATTTCTTTTT-3' (SEQ ID NO: 38) (such a double-stranded probe being particularly intended for the detection of HIV-1M);
5'-AGTCTACCTGACCATGAATTGCTTCCCCTTTTATATGGCAT-3' (SEQ ID NO: 39);
$S_2$-$S'_2$ then representing a fragment of 5'-TAAAAGGGGAAGCAATTCATGGTCAGGTAGACTACAGTCCA-3' (SEQ ID NO: 40) (such a double-stranded probe being particularly intended for the detection of HIV-1O);
5'-CTGAATATTGTCAGAATAGTGAGCGTGCCTTACCGACGATA-3' (SEQ ID NO: 84);
$S_2$-$S'_2$ then representing a fragment of 5'-TATCGTCGGTAAGGCACGCTCACTATTCTGACAATATTCAG-3' (SEQ ID NO: 85) (such a double-stranded probe being particularly intended for the detection of *Salmonella typhi*).

The present invention also relates to the following double-stranded probe as defined above, which can be used for the detection of HBV, said double-stranded probe being constituted of:
a first nucleic acid strand of formula $X_1$-$L_1$-$S_1$-$S'_1$-$Y_1$, in the 5' to 3' orientation, and
a second nucleic acid strand of formula $X_2$-$L_2$-$S_2$-$S'_2$-$Y_2$, in the 5' to 3' orientation;
and wherein:
$X_1$ and $X_2$ are selected from the group constituted of FAM, Atto532, NK141, NK230 and Atto647N;
$Y_1$ and $Y_2$ represent Dabcyl;
$L_1$ and $L_2$ represent 5'-TTTT-3' (SEQ ID NO: 41);
$S_1$ represents 5'-GGAGTTCTTCTTCTAGGG-3' (SEQ ID NO: 42);
$S'_1$ represents 5'-GACC-3' (SEQ ID NO: 43);
$S_2$ represents 5'-CCCTAGAAGAAGAACTCC-3' (SEQ ID NO: 44);
$S'_2$ represents 5'-CTCG-3' (SEQ ID NO: 45);
such a double-stranded probe being particularly intended for the detection of HBV B Zone;
or wherein:
$X_1$ and $X_2$ are selected from the group constituted of FAM, Atto532, NK141, NK230 and Atto647N;
$Y_1$ and $Y_2$ represent Dabcyl;
$L_1$ and $L_2$ represent 5'-TTTTTT-3' (SEQ ID NO: 46);
$S_1$ represents 5'-GGGAGTTCTTCTTC-3' (SEQ ID NO: 47);
$S'_1$ represents 5'-TAGGGG-3' (SEQ ID NO: 48);
$S_2$ represents 5'-GAAGAAGAACTCCC-3' (SEQ ID NO: 49);
$S'_2$ represents 5'-TCGCCT-3' (SEQ ID NO: 50);
such a double-stranded probe being particularly intended for the detection of HBV B Zone;
or wherein:
$X_1$ and $X_2$ are selected from the group constituted of FAM, Atto532, NK141, NK230 and Atto647N;
$Y_1$ and $Y_2$ represent Dabcyl;
$L_1$ and $L_2$ represent 5'-TTTTTT-3' (SEQ ID NO: 46);
$S_1$ represents 5'-CTCTTTACGCGGAC-3' (SEQ ID NO: 51);
$S'_1$ represents 5'-TCCCCG-3' (SEQ ID NO: 52);
$S_2$ represents 5'-GTCCGCGTAAAGAG-3' (SEQ ID NO: 53);
$S'_2$ represents 5'-AGGTGC-3' (SEQ ID NO: 54);
such a double-stranded probe being particularly intended for the detection of HBV A Zone;
or wherein:
$X_1$ and $X_2$ are selected from the group constituted of FAM, Atto532, NK141, NK230 and Atto647N;
$Y_1$ and $Y_2$ represent Dabcyl;
$L_1$ and $L_2$ represent 5'-TTTT-3' (SEQ ID NO: 41);
$S_1$ represents 5'-CTCTCTTTACGCGGACTC-3' (SEQ ID NO: 76);
$S'_1$ represents 5'-CCCG-3' (SEQ ID NO: 77);
$S_2$ represents 5'-GAGTCCGCGTAAAGAGAG-3' (SEQ ID NO: 78);
$S'_2$ represents 5'-GTGC-3' (SEQ ID NO: 79);
such a double-stranded probe being particularly intended for the detection of HBV A Zone.

The present invention also relates to the following double-stranded probe as defined above, which can be used for the detection of HIV, wherein said double-stranded probe is constituted of:
a first nucleic acid strand of formula $X_1$-$L_1$-$S_1$-$S'_1$-$Y_1$, in the 5' to 3' orientation, and
a second nucleic acid strand of formula $X_2$-$L_2$-$S_2$-$S'_2$-$Y_2$, in the 5' to 3' orientation; and wherein:
$X_1$ and $X_2$ are selected from the group constituted of FAM, Atto532, NK141, NK230 and Atto647N;
$Y_1$ and $Y_2$ represent Dabcyl;
$L_1$ and $L_2$ represent 5'-TTTT-3' (SEQ ID NO: 41);

S$_1$ represents 5'-CCAGCTGTGATAAATG-3' (SEQ ID NO: 55);
S'$_1$ represents 5'-TCAG-3' (SEQ ID NO: 56);
S$_2$ represents 5'-CATTTATCACAGCTGG-3' (SEQ ID NO: 57);
S'$_2$ represents 5'-CTAC-3' (SEQ ID NO: 58);
such a double-stranded probe being particularly intended for the detection of HIV-1M;
or wherein:
X$_1$ and X$_2$ are selected from the group constituted of FAM, Atto532, NK141, NK230 and Atto647N;
Y$_1$ and Y$_2$ represent Dabcyl;
L$_1$ and L$_2$ represent 5'-TTTT-3' (SEQ ID NO: 41);
S$_1$ represents 5'-CTGACCATGAATTGCTTC-3' (SEQ ID NO: 59);
S'$_1$ represents 5'-CCCT-3' (SEQ ID NO: 60);
S$_2$ represents 5'-GAAGCAATTCATGGTCAG-3' (SEQ ID NO: 61);
S'$_2$ represents 5'-GTAG-3' (SEQ ID NO: 62);
such a double-stranded probe being particularly intended for the detection of HIV-1O.

The present invention also relates to the following double-stranded probe as defined above, which can be used for the detection of an internal control, wherein said double-stranded probe is constituted of:
a first nucleic acid strand of formula X$_1$-L$_1$-S$_1$-S'$_1$-Y$_1$, in the 5' to 3' orientation, and
a second nucleic acid strand of formula X$_2$-L$_2$-S$_2$-S'$_2$-Y$_2$, in the 5' to 3' orientation;
and wherein:
X$_1$ and X$_2$ are selected from the group constituted of FAM, Atto532, NK141, NK230 and Atto647N;
Y$_1$ and Y$_2$ represent Dabcyl;
L$_1$ and L$_2$ represent 5'-TTTTTT-3' (SEQ ID NO: 46);
S$_1$ represents 5'-AAGCGGTGGCGGCG-3' (SEQ ID NO: 63);
S'$_1$ represents 5'-GAGGAC-3' (SEQ ID NO: 64);
S$_2$ represents 5'-CGCCGCCACCGCTT-3' (SEQ ID NO: 65)';
S'$_2$ represents 5'-GGCGAT-3' (SEQ ID NO: 66);
or wherein:
X$_1$ and X$_2$ are selected from the group constituted of FAM, Atto532, NK141, NK230 and Atto647N;
Y$_1$ and Y$_2$ represent Dabcyl;
L$_1$ and L$_2$ represent 5'-TTTT-3' (SEQ ID NO: 41);
S$_1$ represents 5'-AAGCGGTGGCGGCGGA-3' (SEQ ID NO: 80);
S'$_1$ represents 5'-GGAC-3' (SEQ ID NO: 81);
S$_2$ represents 5'-TCCGCCGCCACCGCTT-3' (SEQ ID NO: 82);
S'$_2$ represents 5'-GGCG-3' (SEQ ID NO: 83).

The present invention also relates to the following double-stranded probe as defined above, which can be used for the detection of *Salmonella typhi*, wherein said double-stranded probe is constituted of:
a first nucleic acid strand of formula X$_1$-L$_1$-S$_1$-S'$_1$-Y$_1$, in the 5' to 3' orientation, and
a second nucleic acid strand of formula X$_2$-L$_2$-S$_2$-S'$_2$-Y$_2$, in the 5' to 3' orientation;
and wherein:
X$_1$ and X$_2$ are selected from the group constituted of FAM, Atto532, NK141, NK230 and Atto647N;
Y$_1$ and Y$_2$ represent Dabcyl;
L$_1$ and L$_2$ represent 5'-TTT-3' (SEQ ID NO: 86);
S$_1$ represents 5'-GAATAGTGAGCGTGCCT-3' (SEQ ID NO: 87);
S'$_1$ represents 5'-TACCG-3' (SEQ ID NO: 88);
S$_2$ represents 5'-AGGCACGCTCACTATTC-3' (SEQ ID NO: 89);
S'$_2$ represents 5'-TGACA-3' (SEQ ID NO: 90).

The invention further relates to a kit for the fluorescent detection of at least one single-stranded or double-stranded target nucleic acid comprising a first nucleic acid strand of formula X$_1$-(L$_1$)$_a$-S$_1$-S'$_1$-(L'$_1$)$_b$-Y$_1$ as defined above, and a second nucleic acid strand of formula X$_2$-(L$_2$)$_c$-S$_2$-S'$_2$-(L'$_2$)$_d$-Y$_2$ as defined above.

The invention also relates to the use of a double-stranded probe according to the invention, for fluorescently detecting single-stranded or double-stranded target nucleic acids, in particular in methods comprising at least one step of nucleic acid hybridization.

In a preferred embodiment of the above-defined use, the target nucleic acid is present in a biological sample.

In another preferred embodiment of the above-defined use, the detection of the at least one single-stranded or double stranded nucleic acid is carried out in an enzyme-based nucleic acid amplification method.

The expression "enzyme-based nucleic acid amplification method" relates to any method wherein enzyme-catalyzed nucleic acid synthesis occurs.

Such an enzyme-based nucleic acid amplification method can be preferentially selected from the group constituted of LCR, Q-beta replication, NASBA, LLA (Linked Linear Amplification), TMA, 3SR, Polymerase Chain Reaction (PCR), notably encompassing all PCR based methods known in the art, such as reverse transcriptase PCR (RT-PCR), simplex and multiplex PCR, real time PCR, end-point PCR, quantitative or qualitative PCR and combinations thereof. These enzyme-based nucleic acid amplification method are well known to the man skilled in the art and are notably described in Saiki et al. (1988) *Science* 239:487, EP 200 362 and EP 201 184 (PCR); Fahy et al. (1991) *PCR Meth. Appl.* 1:25-33 (3SR, Self-Sustained Sequence Replication); EP 329 822 (NASBA, Nucleic Acid Sequence-Based Amplification); U.S. Pat. No. 5,399,491 (TMA, Transcription Mediated Amplification), Walker et al. (1992) *Proc. Natl. Acad. Sci. USA* 89:392-396 (SDA, Strand Displacement Amplification); EP 0 320 308 (LCR, Ligase Chain Reaction); Bustin & Mueller (2005) *Clin. Sci.* (London) 109:365-379 (real-time Reverse-Transcription PCR).

Preferably, the enzyme-based nucleic acid amplification method is selected from the group consisting of Polymerase Chain Reaction (PCR) and Reverse-Transcriptase-PCR (RT-PCR), multiplex PCR or RT-PCR and real time PCR or RT-PCR. Most preferably, the enzyme-based nucleic acid amplification method is a real time, optionally multiplex, PCR or RT-PCR method.

As intended herein "multiplex" relates to the detection of at least two different nucleic acid targets by using at least two doubled-stranded probes according to the invention wherein each one of said target nucleic acids is liable to be detected by at least one of said double-stranded probes. Preferably, the labelling of each probe with a different fluorescent donor makes it possible to detect separately the signal emitted by the distinct probes bound to their target nucleic acid.

In another embodiment, the above-defined use is applied to the fluorescent quantification of the at least one single-stranded or double-stranded nucleic acid target. This may be readily achieved by one skilled in the art by implementing an internal quantification control or by using standard curves.

The present invention also relates to a kit for the fluorescent detection of at least one single-stranded or double-stranded target nucleic acid in an enzyme-based nucleic acid amplification method, comprising:

at least one double-stranded probe as defined above;
an enzyme for enzyme-based nucleic acid amplification;
a reagent mixture adapted for enzyme-based nucleic acid amplification.

In a preferred embodiment, the above-defined kit for the fluorescent detection of at least one single-stranded or double-stranded target nucleic acid in an enzyme-based nucleic acid amplification method further comprises nucleotide primers adapted for enzyme-based amplification of the target nucleic acid.

In another preferred embodiment, the above-defined kit for the fluorescent detection of at least one single-stranded or double-stranded target nucleic acid in an enzyme-based nucleic acid amplification method, is more particularly adapted for the detection of several single-stranded or double-stranded target nucleic acids in a multiplex enzyme-based nucleic acid amplification method, said kit comprising several double-stranded probes as defined above, wherein each of said target nucleic acids is liable to be detected by at least one of said double-stranded probes.

The present invention also relates to a method for detecting at least one single-stranded or double-stranded target nucleic acid in an enzyme-based nucleic acid amplification method, comprising the following steps:
a) mixing at least one single-stranded or double-stranded target nucleic acid with:
    at least one double-stranded probe as defined above intended for the detection of said target nucleic acid, or at least a pair of the two nucleic acid strands as defined in the above kit,
    an enzyme for enzyme-based nucleic acid amplification,
    nucleotide primers adapted for enzyme-based amplification of the target nucleic acid,
    a reagent mixture adapted for enzyme-based nucleic acid amplification, to obtain a reaction mixture;
b) melting nucleic acids present in the reaction mixture by heating said reaction mixture;
c) allowing the double-stranded probe and the nucleotide primers to hybridize to the target nucleic acids by cooling the reaction mixture;
d) allowing the enzyme to catalyze nucleic acid synthesis;
e) repeating steps b) to d);
wherein intensity of fluorescence emission from the reaction mixture is measured in at least one of steps b) to d) and steps b) to d) are repeated at least until the intensity of florescence emission is measured above a background level.

As intended herein, the above steps c) and d) can proceed concomitantly.

In an embodiment of the above-defined method for detecting at least one single-stranded or double-stranded target nucleic acid in an enzyme-based nucleic acid amplification method, the at least one single-stranded or double-stranded target nucleic acid is detected in real-time.

In another embodiment of the above-defined method for detecting at least one single-stranded or double-stranded target nucleic acid in an enzyme-based nucleic acid amplification method the at least one single-stranded or double-stranded target nucleic acid is quantified.

The invention will be further illustrated by the following examples.

EXAMPLES

Example 1

Oligonucleotide Synthesis

Figure 1:
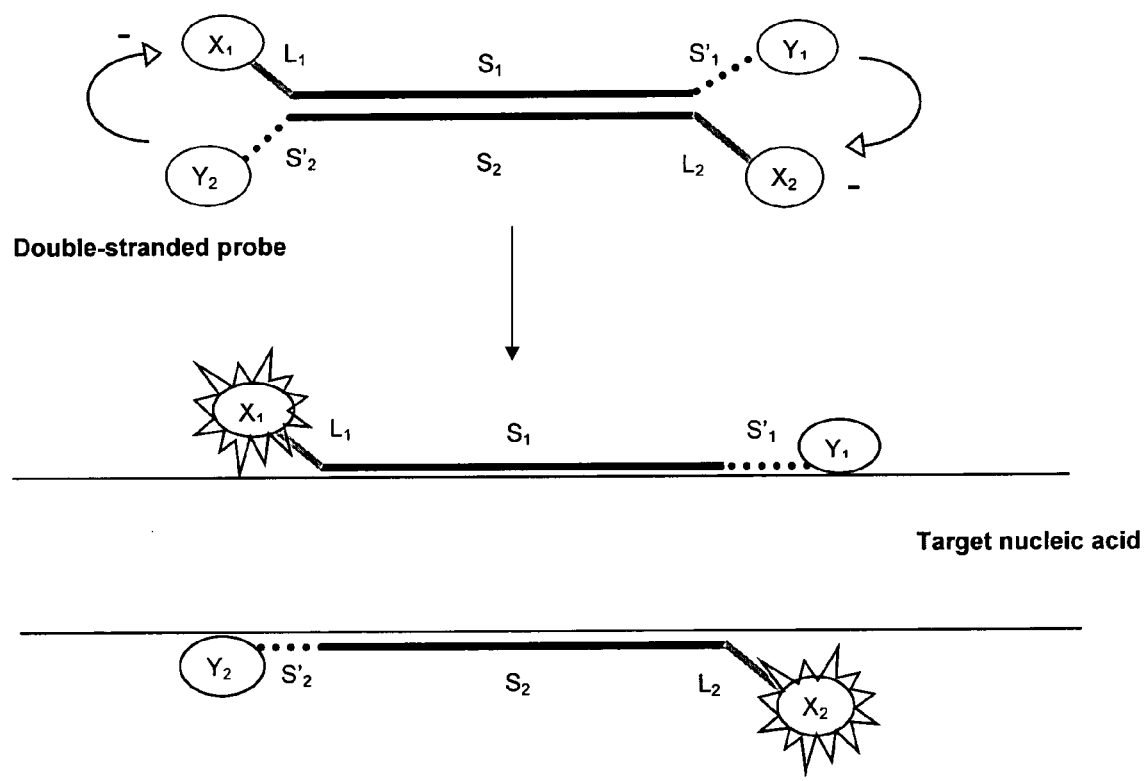
FIG. 1 represents a general scheme of a double-stranded probe according to the invention and its binding to a target nucleic acid. $X_1$ and $X_2$ are fluorophors, $Y_1$ and $Y_2$ quenchers.
Figure 2:
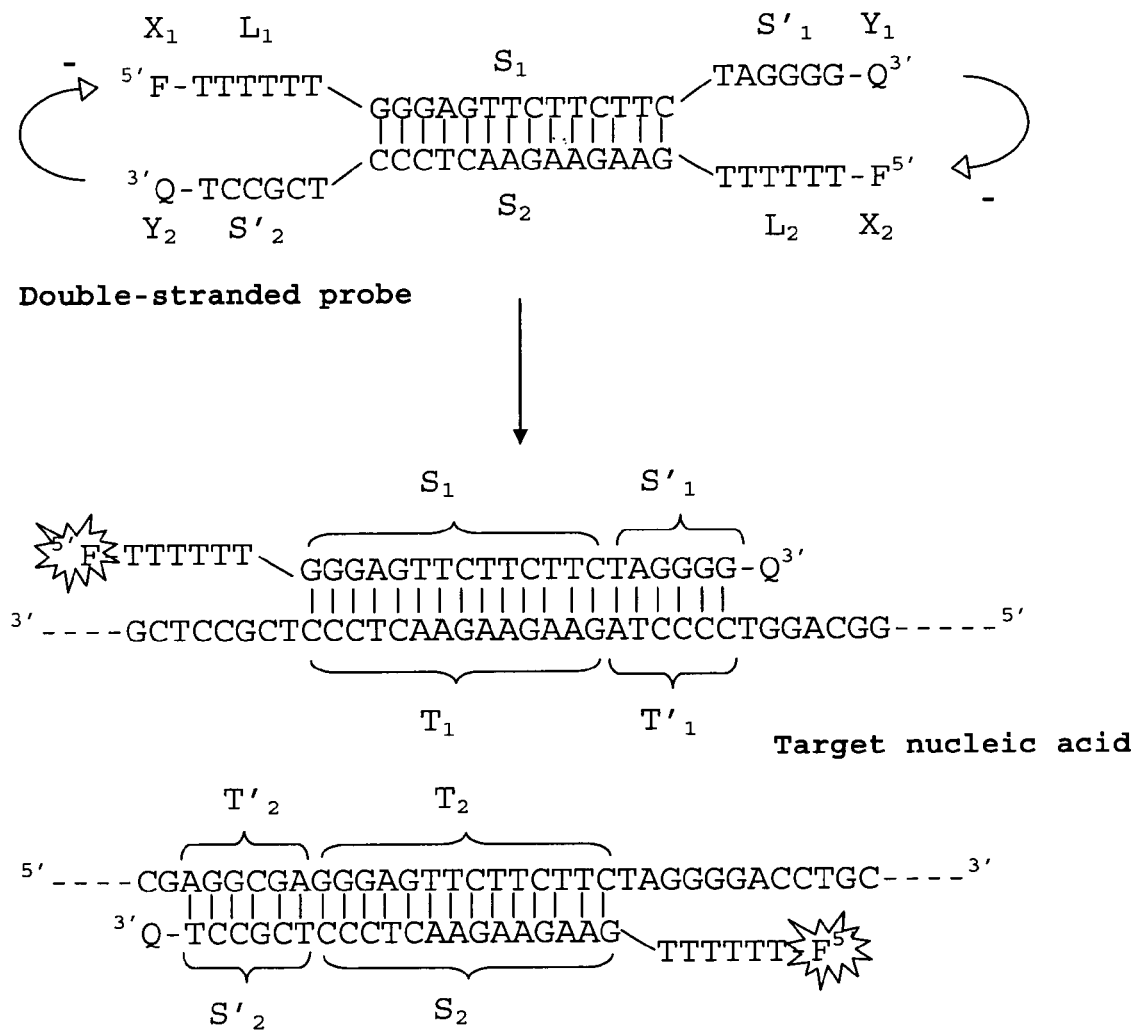
FIG. 2 represents an example of a double-stranded probe ($X_1$-$L_1$-$S_1$-$S'_1$-$Y_1$ (SEQ ID NO:6) and $X_2$-$L_2$-$S_2$-$S'_2$-$Y_2$ (SEQ ID NO:7)) according to the invention and its binding to a target nucleic acid ($T'_1$-$T_1$ (SEQ ID NO:91) and $T'_2$-$T_2$ (SEQ ID NO:92)). F represents a fluorophor, Q a quencher.

The oligonucleotides used were purchased from Eurogentec or synthesized on an Expedite 8909 DNA/RNA synthesizer (Perkin-Elmer), using conditions recommended by the manufacturer and reagents purchased from Applied Biosystems and from Glen Research.

The oligonucleotide probes contained a Dabcyl fluorescent acceptor at the 3' end and a fluorescein (FAM) or Atto532 fluorophor moiety at the 5' end.

The Dabcyl moiety was introduced during the automated oligonucleotide synthesis using a controlled-pore glass column (3'Dabcyl-CPG from Glen Research).

The 5' end of the oligonucleotide was then functionalized using a specific 5'-Thiol Modifier linker from Glen Research.

The oligonucleotide was then purified using high performance liquid chromatography (HPLC). After purification, the protective group was removed from the sulphydryl group at the 5' end and the oligonucleotide 5'SH end was coupled to a fluorescein (FAM) iodoacetamide derivative (6-IAF from Molecular Probes, ref. I-30452) or a Atto532 maleimide derivative (Atto-TEC, ref. AD532-4).

Unreacted dyes were removed by exclusion chromatography with a NAP-5 column (Pharmacia, Sweden).

Finally, the double-labelled oligonucleotide was purified by HPLC, desalted and lyophilized, according to procedures well known to one skilled in the art.

Experimental Determination of the Melting Temperatures (Tm) of the Double-Stranded Probes Melting temperatures were measured by monitoring fluorescence as a function of temperature.

Briefly, thermal denaturation profiles for hybrids labelled with a FAM fluorophor (excitation at 490 nm, emission at 530 nm) were obtained using a Varian spectrofluorimeter (ref. 85-102023-00, Cary Eclipse Bio). All measures were made in the following hybridization buffer: 2.5 mM $MgCl_2$ (ref. 11558147, Qiagen), PCR buffer 1× (PCR buffer 10×, ref. 12182201, Qiagen). Concentration of the FAM-labelled oligonucleotides was 0.1 µM and concentration of the target oligonucleotides was 0.2 µM, in a final volume of 50 µl. The temperature was increased in steps of 0.5° C., from 25 to 95° C., with each step lasting 60 seconds. Fluorescence was measured during the final 30 seconds. The excitation and emission slits were 10 nm and the PMT (photomultiplier) voltage was set to 600V.

All duplexes solutions were treated before denaturation experiments to favour hybridization with the following procedure: heating at 95° C. during 30 minutes, cooling at room temperature during 180 minutes and storage at 4° C. overnight.

Tm were calculated using the first derivative method with the Eclipse Thermal software (Varian).

At room temperature, the two strands of the double-stranded probes are annealed. Low fluorescence is observed (Dabcyl and FAM are in close proximity). As the temperature increase, the hybrids melt apart, Dabcyl is displaced from FAM and quenching diminishes, resulting in an increase in intensity of fluorescence emission from FAM. On the contrary, when a strand of a double-stranded probe is annealed with its target at room temperature, FAM is separated from the Dabcyl which results in a high fluorescence signal. As the temperature increase, hybrids melt apart and the fluorescence signal decreases.

The Tm values measured (Exp. Tm) are indicated in the table below.

|  | Exp. Tm (° C.) | Theo. Tm (° C.) | Exp. Δ Tm | Theo. Δ Tm | Best Ta (° C.) |
|---|---|---|---|---|---|
| SEQ ID NO: 2 + SEQ ID NO: 3 | 59.10 | 52.63 | / | / | 55 |
| SEQ ID NO: 2 + target | 64.90 | 59.54 | 5.80 | 6.91 |  |
| SEQ ID NO: 3 + target | 66.00 | 59.54 | 6.90 | 6.91 |  |
| SEQ ID NO: 6 + SEQ ID NO: 7 | 44.97 | 42.00 | / | / | 50 |
| SEQ ID NO: 6 + target | 60.95 | 57.45 | 15.98 | 15.45 |  |
| SEQ ID NO: 7 + target | 68.54 | 57.45 | 23.57 | 15.45 |  |

The theoretical melting temperatures (Theo. Tm) were calculated using the Tm calculator from OligoAnalyzer 3.0 in SciTools (Integrated DNA Technologies).

Experimental Tm values are slightly higher than theoretical Tm values. The difference between the Tm for the double-stranded probe and the Tm for the hybrid of each strand of the double-stranded probe with its cognate target is similar in practice (Exp. ΔTm) and in theory (Theo. ΔTm). The Tm values were used to determine the best annealing temperature (Best Ta) in the following PCR experiments. The annealing temperature was usually chosen higher than the Tm for double-stranded probe and lower than the Tm for the hybrid of each strand of the double-stranded probes with their respective targets.

NB: Only theoretical Tm values were determined for the following probes:

|  | Theo. Tm (° C.) | Theo. Δ Tm | Best Ta (° C.) |
|---|---|---|---|
| SEQ ID NO: 9 + SEQ ID NO: 10 | 44.0 | / | 50 |
| SEQ ID NO: 9 + target | 61.6 | 17.6 |  |
| SEQ ID NO: 10 + target | 59.5 | 15.5 |  |
| SEQ ID NO: 14 + SEQ ID NO: 15 | 50 | / | 55 |
| SEQ ID NO: 14 + target | 65.5 | 15.5 |  |
| SEQ ID NO: 15 + target | 65.5 | 15.5 |  |

Example 2

Detection of HBV Genome by Targeting the 3' End-Part of the HBV C Gene (B Zone) and the Beginning of HBV DNA Polymerase Encoding Region Double-stranded probes according to the invention were first tested in a real-time Polymerase Chain Reaction (PCR) assay for the detection of the B zone (nucleotides (nt) 2300-2435 of reference strain adw n° M98077) of the HBV genome and compared to a reference Molecular Beacon probe.

Materials and Methods

Genomic HBV DNA was extracted from the HBV DNA positive control Accurun 325 obtained from BBI Diagnostic (ref. A325-5723) using the QIAamp® DSP Virus Kit (Qiagen, ref 60704) according to the manufacturer's instructions. HBV genomic DNA was diluted in water before use.

Nucleotide probes and primers were ordered from Eurogentec. The following probes and primers were used:

| Probe/Primer sequences |  |
|---|---|
| Molecular Beacon probe |  |
| (SEQ ID NO: 1) | 5'F -TGC GCC GAG GGA GTT CTT CTT CTA GGG GAC GCG CA-Q3' |

| Probe/Primer sequences |  |
|---|---|
| Double-stranded probe |  |
| (SEQ ID NO: 2) | 5'F -T TTT-GGA GTT CTT CTT CTA GGG-GAC C-Q3' |
| (SEQ ID NO: 3) | 3'Q-G CTC-CCT CAA GAA GAA GAT CCC-TTT T-F5' |
| HBV-B primer 1 |  |
| (SEQ ID NO: 4) | 5'-CCA CCA AAT GCC CCT ATC TTA TC-3' |
| HBV-B primer 2 |  |
| (SEQ ID NO: 5) | 5'-GAG ATT GAG ATC TTC TGC GAC G-3' |

F = FAM; Q = Dabcyl; the sequences which bind to the target nucleic acid are represented in bold The PCR mixes were as follows: HBV DNA 0-50,000 copies per PCR, Molecular Beacon probe 0.6 µM or double-stranded probe 0.3 µM of each strand, HBV primers 0.6 µM, HotStarTaq® Polymerase (QIAGEN ref 203205) 2.5 U, MgCl$_2$ 6 mM, d(ACGU)TP 200 µM, dTTP 100 µM, 0.25 U UDG, PVP 0.3%, glycerol 5%.

Real time PCR was conducted on a BioRad Chromo4 fluorescent thermocycler with the following thermoprofile:

10 min at 37° C. (uracil-DNA-Glycosylase (UDG) action)
15 min at 95° C. (HotStarTaq ® polymerase activation)
15 sec at 95° C.
30 sec at 55° C. (annealing)  } 50 PCR cycles
30 sec at 72° C.
20° C.

Results

Several parameters were studied in order to compare the double-stranded probes according to the invention and the reference Molecular Beacon probes:

- the threshold cycle (Ct) was evaluated for various starting amounts of DNA in the mixes; Ct represents the number of cycles which are necessary to yield a fluorescence signal higher than background fluorescence; Ct values are proportional to the $\log_{10}$ of the starting amounts of DNA;
- the limit of detection correspond to the lowest quantity of DNA detected
- the linearity of the curve of Ct versus initial DNA quantity in the PCR mixes (a correlation coefficient of at least 0.95 is targeted);
- fluorescence intensity levels and the difference between background fluorescence and fluorescence emission by the probes (the more the difference is important the more the discrimination of small numbers of DNA copies is simple and significant).

Mean Ct is calculated from the different Ct values measured for a given initial number of target DNA copies, SD represents standard deviation and CV the variation coefficient.

The results obtained for the reference Molecular Beacon probe and the double-stranded probe according to the invention are presented in the following tables.

Reference Molecular Beacon (MB) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 6.74E−03 | | | 0.006 |
| 0 | 0 | | | | 0.010 |
| 5 | 36.14 | 37.57 | 1.25 | 3.34% | 0.738 |
| 5 | 38.09 | | | | 0.609 |
| 5 | 38.48 | | | | 0.621 |
| 10 | 37.29 | 35.99 | 1.15 | 3.18% | 0.715 |
| 10 | 35.53 | | | | 0.795 |
| 10 | 35.14 | | | | 0.846 |
| 50 | 33.38 | 33.79 | 0.57 | 1.70% | 0.922 |
| 50 | 34.19 | | | | 0.890 |
| 500 | 31.13 | 30.71 | 0.59 | 1.93% | 1.058 |
| 500 | 30.29 | | | | 1.101 |
| 5000 | 27.14 | 27.04 | 0.15 | 0.55% | 1.279 |
| 5000 | 26.93 | | | | 1.283 |
| 50000 | 23.54 | 23.69 | 0.21 | 0.87% | 1.268 |
| 50000 | 23.83 | | | | 1.347 |

Double-stranded (DS) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 6.74E−03 | | | 0.006 |
| 0 | 0 | | | | 0.004 |
| 5 | 35.26 | 36.49 | | | 1.125 |
| 5 | 0 | | | | 0.004 |
| 5 | 37.72 | | | | 0.921 |
| 10 | 34.81 | 35.15 | 0.34 | 0.97% | 1.087 |
| 10 | 35.15 | | | | 1.121 |
| 10 | 35.49 | | | | 1.041 |
| 50 | 33.84 | 33.50 | 0.49 | 1.46% | 1.209 |
| 50 | 33.15 | | | | 1.209 |
| 500 | 30.12 | 30.59 | 0.66 | 2.15% | 1.478 |
| 500 | 31.05 | | | | 1.419 |
| 5000 | 26.58 | 26.71 | 0.18 | 0.69% | 1.652 |

| Initial number of target DNA copies/PCR | Ct | Mean Ct | SD | CV | Maximum Fluorescence |
|---|---|---|---|---|---|
| 5000 | 26.84 | | | | 1.482 |
| 50000 | 23.67 | 23.10 | 0.81 | 3.52% | 1.710 |
| 50000 | 22.52 | | | | 1.689 |

The fluorescence gain obtained by using the double-stranded probe of the invention is summarized in the following table:

| Initial number of target DNA copies/PCR | Ct MB/Ct DS | Fluorescence gain (%) |
|---|---|---|
| 5 | 0.97 | 55.9 |
| 10 | 0.98 | 37.9 |
| 50 | 0.99 | 33.4 |
| 500 | 1.00 | 34.2 |
| 5000 | 0.99 | 22.3 |
| 50000 | 0.98 | 30.0 |
| | | Mean: 35.6% |

Fluorescence gain is calculated with the following formula: [(Max. fluorescence DS − Max. fluorescence MB)/Max. fluorescence MB] × 100

The Ct values measured using the double-stranded probe according to the invention are similar to those measured with the reference Molecular Beacon probe.

The sensitivity is similar using both probes, but a 35.6% increase in maximum fluorescence is obtained on average when using the double-stranded probe according to the invention.

As for the reference Molecular Beacon probe, the linear regression of Ct with respect to the initial number of target DNA copies for the double-stranded probe according to the invention presents a high correlation coefficient ($R^2=0.9788$).

Real-time PCRs using double-stranded probes according to the invention remain functional within a wide range of annealing temperatures (from 51° C. to 60° C.).

Indeed, similar results were obtained when the double-stranded probes was tested with an annealing temperature of 51 and 60° C. (see table below).

Double-stranded probe (Ta=51° C.):

| Initial number of target DNA copies/PCR | Ct | MeanCt | SD | CV | Maximum Fluorescence |
|---|---|---|---|---|---|
| 0 | 0 | Threshold fluorescence value: 4.52E−02 | | | 0.004 |
| 0 | 0 | | | | 0.004 |
| 5 | 0 | 36.08 | | | 0.009 |
| 5 | 36.08 | | | | 1.119 |
| 50 | 32.38 | 32.53 | 0.21 | 0.63% | 1.424 |
| 50 | 32.67 | | | | 1.393 |
| 5000 | 25.04 | 25.18 | 0.19 | 0.76% | 1.859 |
| 5000 | 25.31 | | | | 1.805 |

Double-stranded probe (Ta=60° C.):

| Initial number of target DNA copies/PCR | Ct | MeanCt | SD | CV | Maximum Fluorescence |
|---|---|---|---|---|---|
| 0 | 0 | Threshold fluorescence value: 1.11E−02 | | | 0.013 |
| 0 | 0 | | | | 0.012 |
| 5 | 38.96 | 38.96 | | | 0.388 |

-continued

| Initial number of target DNA copies/PCR | Ct | MeanCt | SD | CV | Maximum Fluorescence |
|---|---|---|---|---|---|
| 5 | 0 | | | | 0.009 |
| 50 | 35.01 | 35.12 | 0.15 | 0.42% | 0.545 |
| 50 | 35.22 | | | | 0.518 |
| 5000 | 27.86 | 27.74 | 0.17 | 0.61% | 0.790 |
| 5000 | 27.62 | | | | 0.750 |

Besides, a real-time PCR carried out with the same double-stranded probe, at a lower concentration of 0.2 µM of each strand yielded similar results (as compared to a concentration of 0.6 µM of the reference Molecular Beacon probe).

Example 3

Detection of the B Zone of HBV Genome

An alternative double-stranded probe according to the invention was designed and used in the same conditions as set out in Example 2, except for the annealing temperature, which was set at 50° C., and compared to a Molecular Beacon probe.

```
           Probe/Primer sequences

Double-stranded
probe (SEQ ID NO: 6)    5'F-TTT TTT-GGG AGT TCT TCT TC-
                    TAG GGG-Q3'

(SEQ ID NO: 7)    3'Q-TCC GCT-CCC TCA AGA AGA AG-
                    TTT TTT-F5'
```

F = FAM; Q = Dabcyl; the sequences which bind to the target nucleic acid are represented in bold Double-stranded (DS) probe (Ta=50° C.):

| Initial number of target DNA copies/PCR | Ct | Mean Ct | SD | CV | Maximum Fluorescence |
|---|---|---|---|---|---|
| 0 | 0 | Threshold fluorescence value: 1.36E−02 | | | 0.013 |
| 0 | 0 | | | | 0.026 |
| 5 | 38.10 | 37.86 | 0.66 | 1.74% | 0.737 |
| 5 | 38.36 | | | | 0.712 |
| 5 | 37.11 | | | | 0.817 |
| 10 | 36.81 | 37.00 | 0.27 | 0.73% | 0.825 |
| 10 | (39.89) | | | | 0.665 |
| 10 | 37.19 | | | | 0.718 |
| 50 | 35.19 | 34.63 | 0.79 | 2.29% | 0.893 |
| 50 | 34.07 | | | | 0.797 |
| 500 | 31.44 | 31.26 | 0.25 | 0.81% | 1.015 |
| 500 | 31.08 | | | | 0.998 |
| 5000 | 27.72 | 27.86 | 0.20 | 0.71% | 1.125 |
| 5000 | 28.0 | | | | 1.024 |
| 50000 | 23.73 | 23.96 | 0.32 | 1.33% | 1.108 |
| 50000 | 24.18 | | | | 1.072 |

As for the double-stranded probe set out in Example 1, the Ct measured using the double-stranded probe according to the invention are similar to those measured with the reference Molecular Beacon probe.

Again, the sensitivity is similar using both probes.

As for the reference Molecular Beacon probe, the linear regression of Ct with respect to the initial number of target DNA copies also presents a high correlation coefficient ($R^2$=0.9746) for the double stranded probe according to the invention.

Real-time PCRs using this double-stranded probe remain functional within a wide range of annealing temperatures (from 46° C. to 55° C.). Similar results were obtained when the double-stranded probes was tested with an annealing temperature of 55° C. (see table below).

Double-stranded probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 6.74E−03 | | | 0.016 |
| 0 | 0 | | | | 0.005 |
| 5 | 36.31 | 36.31 | | | 0.583 |
| 5 | 0 | | | | 0.004 |
| 50 | 34.20 | 33.86 | 0.48 | 1.42% | 0.755 |
| 50 | 33.52 | | | | 0.776 |
| 5000 | 26.58 | 26.59 | 0.01 | 0.05% | 1.052 |
| 5000 | 26.60 | | | | 0.998 |

Besides, a real-time PCR carried out with the same double-stranded probe, at a lower concentration of 0.2 µM of each strand yielded similar results (as compared to a concentration of 0.6 µM of the reference Molecular Beacon probe).

Example 4

Detection of HBV Genome by Targeting an Overlapping Region of HBV Genome (A Zone)

Double-stranded probes according to the invention were then tested in a real-time Polymerase Chain Reaction (PCR) assay for the detection of the A zone of the HBV genome (end of HBV DNA polymerase encoding and the beginning of the sequences encoding the HBV X protein-nucleotides (nt) 1440-1602 of reference strain adw n° M98077) and compared to a reference Molecular Beacon probe, using the same conditions than those set out in Example 2 except for the double-stranded probe concentration which was set at 0.2 µM.

The following probes and primers were used:

```
           Probe/Primer sequences

Molecular
Beacon probe (SEQ ID NO: 8)    5' F-CGGCA GGA GTC CGC GTA AAG
                    AGA GGT G TGCCG-Q 3'

Double-stranded
probe (SEQ ID NO: 9)    5' F-TTT TTT CTC TTT ACG CGG AC
                    T CCC CG-Q 3'

(SEQ ID NO: 10)   3' Q-CGT GGA GAG AAA TGC GCC TG
                    T TTT TT-F 5'

HBV-A primer 1

(SEQ ID NO: 11)   5'-GCT GAA TCC CGC GGA CGA-3'

HBV-A primer 2

(SEQ ID NO: 12)   5'-GTG CAG AGG TGA AGC GAA
                    GTG-3'
```

F = FAM; Q = Dabcyl; the sequences which bind to the target nucleic acid are represented in bold The results obtained for the Molecular Beacon probe and the double-stranded probe according to the invention are presented in the following tables.

Reference Molecular Beacon (MB) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 4.09E−03 | | | 0.006 |
| 0 | 0 | | | | 0.002 |
| 5 | 37.24 | 37.24 | | | 0.423 |
| 5 | 0 | | | | 0.003 |
| 5 | 0 | | | | 0.006 |
| 10 | 38.45 | 36.26 | 0.82 | 2.27% | 0.308 |
| 10 | 37.80 | | | | 0.408 |
| 10 | 36.79 | | | | 0.476 |
| 50 | 35.17 | 33.72 | 0.09 | 0.27% | 0.631 |
| 50 | 33.96 | | | | 0.592 |
| 500 | 31.83 | 29.88 | 0.23 | 0.78% | 0.705 |
| 500 | 31.17 | | | | 0.801 |
| 5000 | 27.96 | 27.18 | 0.04 | 0.13% | 1.000 |
| 5000 | 27.70 | | | | 1.031 |
| 50000 | 23.59 | 23.10 | 0.01 | 0.03% | 1.157 |
| 50000 | 23.28 | | | | 1.179 |

Double-stranded (DS) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 1.11E−02 | | | 0.019 |
| 0 | 0 | | | | 0.008 |
| 5 | 38.81 | 38.95 | 0.61 | 1.56% | 0.725 |
| 5 | 38.43 | | | | 0.741 |
| 5 | 39.62 | | | | 0.682 |
| 10 | 39.50 | 39.34 | 0.81 | 2.05% | 0.646 |
| 10 | 40.05 | | | | 0.634 |
| 10 | 38.46 | | | | 0.758 |
| 50 | 36.41 | 36.34 | 0.11 | 0.29% | 0.947 |
| 50 | 36.26 | | | | 0.933 |
| 500 | 32.76 | 32.99 | 0.33 | 0.99% | 1.148 |
| 500 | 33.22 | | | | 1.137 |
| 5000 | 29.06 | 28.61 | 0.64 | 2.25% | 1.463 |
| 5000 | 28.15 | | | | 1.449 |
| 50000 | 24.58 | 24.83 | 0.35 | 1.42% | 1.481 |
| 50000 | 25.08 | | | | 1.458 |

The results are summarized in the following table:

| Initial number of target DNA copies/PCR | Ct MB/Ct DS | Fluorescence gain (%) |
|---|---|---|
| 5 | 1.05 | 73.3 |
| 10 | 1.08 | 71.0 |
| 50 | 1.08 | 53.7 |
| 500 | 1.10 | 51.7 |
| 5000 | 1.05 | 43.4 |
| 50000 | 1.07 | 25.8 |
| | | Mean: 49.1 |

Fluorescence gain is calculated with the following formula: [(Max. fluorescence DS − Max. fluorescence MB)/Max. fluorescence MB] × 100

The Ct measured using the double-stranded probe according to the invention are in line with those measured with the reference Molecular Beacon probe.

The sensitivity is similar using both probes, but a 49.1% increase on average in maximum fluorescence is obtained when using the double-stranded probe according to the invention.

As for the reference Molecular Beacon probe, the linear regression of Ct with respect to the initial number of target DNA copies presents a high correlation coefficient ($R^2$=0.9826) for the double-stranded probe according to the invention.

Real-time PCRs using double-stranded probes according to the invention remain functional within a wide range of annealing temperatures (from 51° C. to 60° C.).

Indeed similar results were obtained when the double-stranded probes was tested with an annealing temperature of 51 and 60° C. (see table below).

Double-stranded probe (Ta=51° C.):

| Initial number of target DNA copies/PCR | Ct | MeanCt | SD | CV | Maximum Fluorescence |
|---|---|---|---|---|---|
| 0 | 0 | Threshold fluorescence value: 1.83E−02 | | | 0.032 |
| 0 | 0 | | | | 0.032 |
| 10 | 39.02 | 38.89 | 0.19 | 0.49% | 0.759 |
| 10 | 38.75 | | | | 0.794 |
| 50 | 37.37 | 37.53 | 0.22 | 0.58% | 0.910 |
| 50 | 37.68 | | | | 0.876 |
| 5000 | 29.97 | 29.95 | 0.04 | 0.12% | 1.364 |
| 5000 | 29.92 | | | | 1.358 |

Double-stranded probe (Ta=60° C.):

| Initial number of target DNA copies/PCR | Ct | MeanCt | SD | CV | Maximum Fluorescence |
|---|---|---|---|---|---|
| 0 | 0 | Threshold fluorescence value: 1.11E−02 | | | 0.015 |
| 0 | 0 | | | | 0.016 |
| 10 | 38.12 | 38.16 | 0.05 | 0.13% | 0.453 |
| 10 | 38.19 | | | | 0.427 |
| 50 | 36.77 | 36.18 | 0.83 | 2.31% | 0.499 |
| 50 | 35.59 | | | | 0.525 |
| 5000 | 29.49 | 29.54 | 0.06 | 0.22% | 0.783 |
| 5000 | 29.58 | | | | 0.727 |

Besides, a real-time PCR carried out with the same double-stranded probe, both at a lower concentration of 0.1 μM and at a higher concentration 0.3 μM of each strand yielded similar results (as compared to a concentration of 0.6 μM of the reference Molecular Beacon probe).

Example 5

Detection of an Internal Control (IC)

A double-stranded probe according to the invention was also tested in a real-time PCR assay for the detection of an internal control (IC) and compared to a reference Molecular Beacon probe.

ICs are used in multiplex assays to validate the PCR results thanks to its target Ct and its confidence interval. Besides it enables the detection of inhibitors in the samples and thus helps validating their quantification. An IC is usually designed to have the same PCR efficiency and the same amplicon length than the target nucleic acid.

The IC presently used is a fragment of 408 nucleotides generated by PCR from the ADH Maize gene (maize GMO standard ERM-BF411a, ref. 91528 Fluka) with the following specific primers:

```
                                              (SEQ ID NO: 18)
    ADH5Fc:    5'-TGC CAT CGC TGT GCT ACA AC-3'

(SEQ ID NO: 19)
    ADH5Rc:    5'-AAC GAC GGG AAG GAG GGT GC-3'
```

The IC fragment DNA was then extracted using the QiaQuick® PCR Purification Kit (Qiagen, ref 28104) according to the manufacturer's instructions. The IC fragment DNA was diluted in water after UV dosage and before use.

The PCR mixes used were as described in Example 2, except for the DNA to be amplified, IC DNA 0-10,000 copies per PCR; the concentration of the probes: Molecular Beacon probe 0.2 µM, double-stranded probe according to the invention 0.1 µM of each strand; and the concentration of the primers 0.3 µM.

The sequences of the probes and primers are set forth below:

| Probe/Primer sequences | |
|---|---|
| Molecular Beacon probe | |
| (SEQ ID NO: 13) | 5' F-TG CTG CGT CCT CCG CCG CCA CCG CTT GGG CAG CA-Q 3' |
| Double-stranded probe | |
| (SEQ ID NO: 14) | 5' F-TT TTT T-AA GCG GTG GCG GCG-GAG GAC-Q 3' |
| (SEQ ID NO: 15) | 3' Q-TA GCG G-TT CGC CAC CGC CGC-TTT TTT-F 5' |
| IC primer 1 | |
| (SEQ ID NO: 16) | 5'-GAG CCG CAG ATC CGA GCT A-3' |
| IC primer 2 | |
| (SEQ ID NO: 17) | 5'-GGA GTG GAA CAT AGC CGT GGT C-3' |

F = Atto532; Q = Dabcyl; the sequences which bind to the target nucleic acid are represented in bold The results obtained for the Molecular Beacon probe and the double-stranded probe according to the invention are presented in the following tables.

Reference Molecular Beacon (MB) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 1.50E−03 | | | 0.002 |
| 0 | 0 | | | | 0.001 |
| 100 | 35.47 | 35.51 | 0.07 | 0.19% | 0.094 |
| | 35.59 | | | | 0.095 |
| | 35.48 | | | | 0.085 |
| 300 | 34.33 | 34.17 | 0.23 | 0.66% | 0.088 |
| | 34.01 | | | | 0.109 |
| | (36.01) | | | | 0.072 |
| 1000 | 32.00 | 32.14 | 0.12 | 0.39% | 0.127 |
| | 32.24 | | | | 0.124 |
| | 32.18 | | | | 0.129 |
| 10000 | 30.11 | 29.46 | 0.56 | 1.92% | 0.165 |
| | 29.18 | | | | 0.168 |
| | 29.09 | | | | 0.163 |

Double-stranded (DS) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 3.03E−02 | | | 0.002 |
| 100 | 38.38 | 38.56 | 0.45 | 1.16% | 0.092 |
| | 39.07 | | | | 0.083 |
| | 38.23 | | | | 0.073 |
| 300 | 37.55 | 36.91 | 0.81 | 2.20% | 0.116 |
| | 36.00 | | | | 0.125 |
| | 37.19 | | | | 0.125 |
| 1000 | 34.36 | 34.48 | 0.27 | 0.77% | 0.129 |
| | 34.29 | | | | 0.148 |
| | 34.78 | | | | 0.146 |
| 10000 | 31.30 | 30.90 | 0.34 | 1.11% | 0.179 |
| | 30.71 | | | | 0.196 |
| | 30.70 | | | | 0.179 |

The results are summarized in the following table:

| Initial number of target DNA copies/PCR | Ct MB/Ct DS | Fluorescence gain (%) |
|---|---|---|
| 100 | 1,09 | −9.5 |
| 300 | 1.08 | 36.1 |
| 1000 | 1.07 | 11.3 |
| 10000 | 1.05 | 11.7 |
| | | Mean: 12.4 |

Fluorescence gain is calculated with the following formula: [(Max. fluorescence DS − Max. fluorescence MB)/Max. fluorescence MB] × 100

The Ct measured using the double-stranded probe according to the invention are similar to those measured with the reference Molecular Beacon probe.

The sensitivity and maximum fluorescence is similar using both probes.

As for the Molecular Beacon probe, the linear regression of Ct with respect to the initial number of target DNA copies presents a high correlation coefficient ($R^2$=0.9767) for the double-stranded probe according to the invention.

Real-time PCRs using double-stranded probes according to the invention remain functional within a wide range of annealing temperatures (from 51° C. to 60° C.).

Indeed, similar results were obtained when the double-stranded probes was tested with an annealing temperature of 51 and 60° C. (see table below).

Double-stranded (DS) probe (Ta=51° C.):

| Initial number of target DNA copies/PCR | Ct | MeanCt | SD | CV | Maximum Fluorescence |
|---|---|---|---|---|---|
| 0 | 0 | Threshold fluorescence value: 3.03E−03 | | | 0.002 |
| 0 | 0 | | | | 0.003 |
| 300 | 32.25 | 32.32 | 0.14 | 0.44% | 0.251 |
| 300 | 32.22 | | | | 0.267 |
| 300 | 32.48 | | | | 0.246 |
| 600 | 31.14 | 31.25 | 0.10 | 0.33% | 0.279 |
| 600 | 31.28 | | | | 0.292 |
| 600 | 31.34 | | | | 0.249 |

Double-stranded (DS) probe (Ta=60° C.):

| Initial number of target DNA copies/PCR | Ct | MeanCt | SD | CV | Maximum Fluorescence |
|---|---|---|---|---|---|
| 0 | 0 | Threshold fluorescence value 3.03E−03 | | | 0.002 |

-continued

| Initial number of target DNA copies/PCR | Ct | MeanCt | SD | CV | Maximum Fluorescence |
|---|---|---|---|---|---|
| 0 | 0 | | | | 0.003 |
| 300 | 32.98 | 32.50 | 0.54 | 1.66% | 0.173 |
| 300 | 31.92 | | | | 0.183 |
| 300 | 32.61 | | | | 0.174 |
| 600 | 31.28 | 30.80 | 0.77 | 2.51% | 0.202 |
| 600 | 31.21 | | | | 0.204 |
| 600 | 29.91 | | | | 0.190 |

Besides, a real-time PCR carried out with the same double-stranded probe, at a lower concentration of 0.1 µM of each strand yielded similar results (as compared to a concentration of 0.2 µM of the reference Molecular Beacon probe).

Multiplex Assay

A multiplex assay combining the detection of the A zone of the HBV genome and of an internal control (enabling the determination of the yield of extraction and of the yield of inhibition during PCR) was set out using the probes and primers of Examples 4 and 5.

Briefly, the following template DNA, probe and primer concentrations were used in the otherwise similar mixes of Example 2:

IC DNA 300 copies per PCR; IC primers 0.3 µM;
HBV DNA 0-50,000 copies per PCR; HBV primers 0.6 µM;
Molecular Beacon IC probe 0.2 µM or double-stranded IC probe 0.1 µM of each strand;
Molecular Beacon HBV probe 0.6 µM or double-stranded HBV probe 0.2 µM of each strand.

The real-time PCR conditions were unchanged as compared to those set out above.

Detection of FAM Fluorescence (HBV DNA Detection):

Reference Molecular Beacon (MB) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 6.74E−03 | | | 0.006 |
| 0 | 0 | | | | 0.006 |
| IC control | 0 | | | | 0.010 |
| IC control | 0 | | | | 0.008 |
| 5 | 39.29 | 39.29 | | | 0.347 |
| 5 | 0 | | | | 0.006 |
| 10 | 40.13 | 39.03 | 1.56 | 3.99% | 0.262 |
| 10 | 37.93 | | | | 0.444 |
| 50 | 34.86 | 34.83 | 0.05 | 0.14% | 0.608 |
| 50 | 34.79 | | | | 0.564 |
| 500 | 33.26 | 32.98 | 0.40 | 1.20% | 0.638 |
| 500 | 32.7 | | | | 0.685 |
| 5000 | 29.83 | 29.50 | 0.47 | 1.61% | 0.884 |
| 5000 | 29.16 | | | | 0.844 |
| 50000 | 25.43 | 25.45 | 0.03 | 0.11% | 1.001 |
| 50000 | 25.47 | | | | 0.946 |

Double-stranded (DS) probe (Ta=55° C.):

| Initial number of target DNA copies/PCR | Ct | Mean Ct | SD | CV | Maximum Fluorescence |
|---|---|---|---|---|---|
| 0 | 0 | Threshold fluorescence value: 1.11E−02 | | | 0.017 |
| | 0 | | | | 0.010 |
| | 0 | | | | 0.012 |
| IC control | 0 | | | | 0.015 |
| | 0 | | | | 0.008 |
| | 39.09 | 38.12 | | | 0.373 |
| 5 | 0 | | | | 0.006 |
| | 37.14 | | | | 0.443 |
| | 0 | 38.73 | | | 0.007 |
| 10 | 39.22 | | | | 0.360 |
| | 38.24 | | | | 0.375 |
| | 35.50 | 35.65 | 0.14 | 0.39% | 0.543 |
| 50 | 35.69 | | | | 0.461 |
| | 35.77 | | | | 0.621 |
| | 31.86 | 32.25 | 0.91 | 2.82% | 0.735 |
| 500 | 33.29 | | | | 0.678 |
| | 31.60 | | | | 0.657 |
| | 29.25 | 29.57 | 0.34 | 1.16% | 0.817 |
| 5000 | 29.52 | | | | 0.890 |
| | 29.93 | | | | 0.873 |
| | 25.04 | 25.26 | 0.35 | 1.37% | 0.985 |
| 50000 | 25.08 | | | | 0.988 |
| | 25.66 | | | | 0.980 |

NB: IC control represent mixes in which 300 copies of IC only were added without any HBV DNA.

The results are summarized in the following table:

| Initial number of target DNA copies/PCR | Ct MB/Ct DS | Fluorescence gain (%) |
|---|---|---|
| 5 | 0.97 | 17.6 |
| 10 | 0.99 | 4.1 |
| 50 | 1.02 | −7.6 |
| 500 | 0.98 | 4.3 |
| 5000 | 1.00 | −0.5 |
| 50000 | 0.99 | 1.1 |
| | | Mean: 0.3 |

Fluorescence gain is calculated with the following formula: [(Max. fluorescence DS − Max. fluorescence MB)/Max. fluorescence MB] × 100

Detection of Atto532 Fluorescence (IC DNA Detection):

As expected this detection yielded essentially constant results for both probe systems. Only a slight decrease in Ct was observed at high concentrations of HBV DNA (50,000 copies/PCR), due to interference between the FAM and Atto532 dyes.

Overall, results obtained for the multiplex assay indicate that double-stranded probes according to the invention are fully functional in such detection systems.

Besides, the results yielded using the double-stranded probe of the invention are similar to those obtained using reference Molecular Beacon probes. Moreover, these results could be achieved with lower concentrations of the double-stranded probes as compared to the Molecular Beacon probes.

Also worth noting, the double-stranded probes according to the invention are functional in a wide range of annealing temperatures. This is particularly advantageous when implementing multiplex assays, wherein the various probes which are used have to be functional at the same annealing temperature.

Finally, the double-stranded probe according to the invention were also shown to be functional in a wide range of $MgCl_2$ concentration (4-7 mM) (see table below).

| | Double-stranded (DS) probe 4 mM MgCl₂ | | | | | Double-stranded (DS) probe 7 mM MgCl₂ | | | | |
|---|---|---|---|---|---|---|---|---|---|---|
| copies/ PCR | Ct | MeanCt | SD | CV | FluoMax | Ct | MeanCt | SD | CV | FluoMax |
| 0 | 0 | Threshold | 0.041 | | 0.038 | 0 | Threshold | 0.041 | | 0.008 |
| | 0 | | | | 0.031 | 0 | | | | 0.011 |
| T IC | 0 | | | | 0.033 | 0 | | | | 0.005 |
| | 0 | | | | 0.012 | 0 | | | | 0.010 |
| 5 | 40.87 | 40.74 | 0.19 | 0.47% | 0.286 | (0) | 41.27 | | | 0.006 |
| | 40.60 | | | | 0.372 | 41.27 | | | | 0.310 |
| 10 | 39.94 | 39.72 | 0.32 | 0.80% | 0.375 | 40.01 | 40.66 | 0.92 | 2.26% | 0.418 |
| | 39.49 | | | | 0.511 | 41.31 | | | | 0.345 |
| 50 | 38.03 | 37.79 | 0.35 | 0.92% | 0.633 | 37.42 | 38.08 | 0.93 | 2.43% | 0.515 |
| | 37.54 | | | | 0.685 | 38.73 | | | | 0.409 |
| 500 | 34.54 | 34.55 | 0.01 | 0.02% | 0.778 | 34.39 | 34.49 | 0.13 | 0.39% | 0.673 |
| | 34.55 | | | | 0.836 | 34.58 | | | | 0.762 |
| 5000 | 31.39 | 31.29 | 0.15 | 0.47% | 0.952 | 31.28 | 31.19 | 0.13 | 0.41% | 0.868 |
| | 31.18 | | | | 0.972 | 31.1 | | | | 0.891 |
| 50000 | 27.89 | 27.78 | 0.16 | 0.56% | 0.958 | 27.70 | 27.54 | 0.23 | 0.85% | 1.062 |
| | 27.67 | | | | 1.013 | 27.37 | | | | 1.052 |

Example 6

Control of the Amplicons

Figure 3:
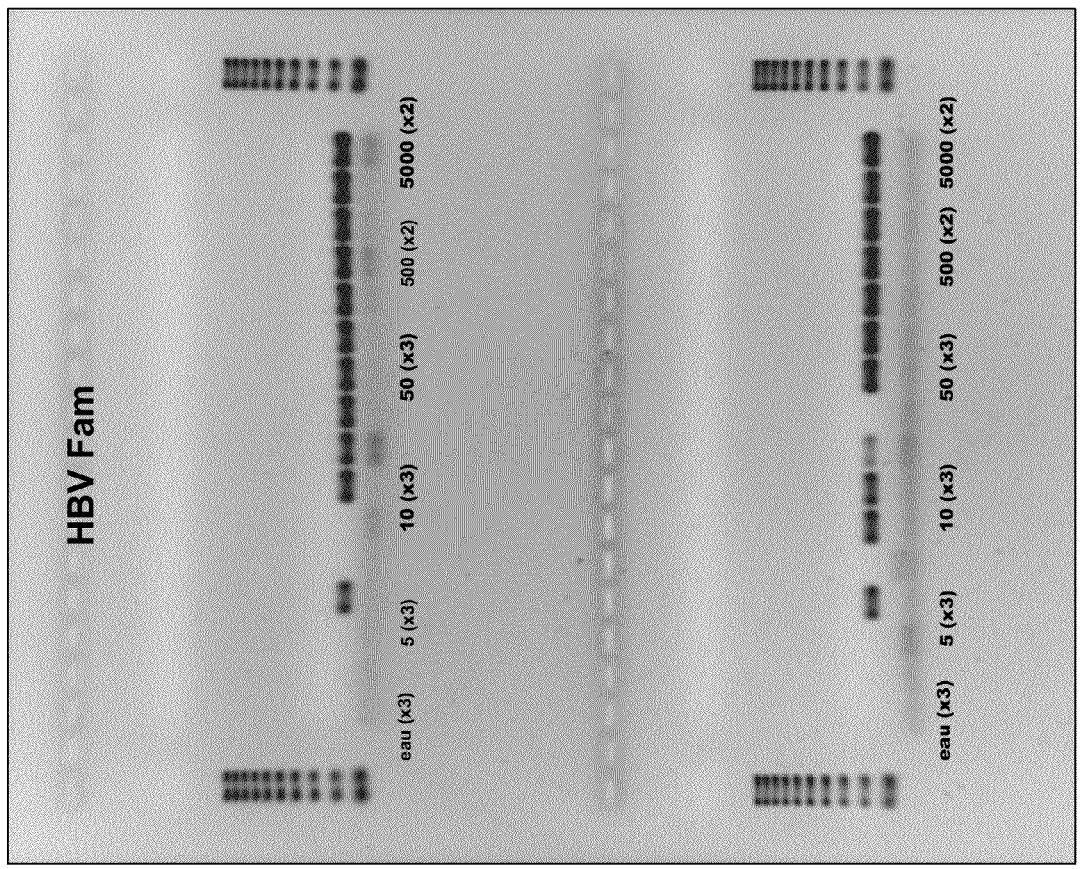
FIG. 3 represents an electrophoretic gel migration (from top to bottom) of PCRs carried out with double-stranded probes according to the invention (upper panel) and with Molecular Beacon probes (lower panel). From left to right, the lanes correspond to:
EZ weight marker—unloaded lane—water control×3 lanes—5 copies HBV/PCR×3 lanes—10 copies HBV/PCR×3 lanes—50 copies HBV/PCR×3 lanes—500 copies HBV/PCR×2 lanes—5000 copies HBV/PCR—2 lanes—unloaded lane—EZ weight marker.

The quality of the PCR products obtained with the above PCR reactions was controlled by agarose gel electrophoresis. The results are presented in FIG. 3.

Only one nucleic acid fragment is amplified by PCR, with the expected size of 163 base pairs, in the presence of the Molecular Beacon probe or in presence of the double-stranded probe. No non-specific amplification is observed. Besides, the use of the double-stranded probes according to the invention does not yield more primer-dimers (MW≤50 bp) as when the Molecular Beacon probes are used.

Example 7

Detection of HIV1-M Genome

The double-stranded probes according to the invention were applied to the real-time PCR detection of the various genotypes (A, B, C, D, E, F, G and H) of HIV-1M and compared to reference Molecular Beacon probes.

Materials and Methods:

The assayed samples were either the supernatant of a culture of lymphoblastoid CEM cells having a viral titer of 7.75 10⁸ viral particles of HIV-1M subtype B/ml or the PRD201 panel (BBI diagnostic) containing 8 genotypes (A, B, C, D, E, F, G and H) of HIV1-M at 50,000 viral particles/ml.

HIV RNA is extracted from the samples using the QIAamp® DSP Virus Kit (QIAGEN, ref. 60704) according to the manufacturer's instructions. The extracted RNA is then diluted in water with carrier RNA (1 ng/ml, QIAGEN, ref. 1009615).

The sequences of the probes and primers used are set forth below:

| Probe/Primer sequences | |
|---|---|
| Molecular Beacon probes HIV-1M | |
| SH1BM14 (SEQ ID NO: 20) | ⁵'F-CGCGC ATA GTG GCC AGC TGT GAT AAA TGT C GCGCG-Q³' |
| SH1BM17 (SEQ ID NO: 21) | ⁵'F-CGCGC ATA GT<u>A</u> GC<u>T</u> TGC TGT GAT AAA TGT C GCGCG- |
| SH1BM18 (SEQ ID NO: 22) | ⁵'F-ATA GT<u>A</u> GCC A<u>A</u>C TGT GAT AAA TGT C GCGCG-Q³' |
| Double-stranded probe HIV-1M | |
| (SEQ ID NO: 23) | ⁵'F-TTTT CCA GCT GTG ATA AAT G TCAG-Q³' |
| (SEQ ID NO: 24) | ³'Q-CATC GGT CGA CAC TAT TTA C TTTT-F⁵' |
| HIV-1M primer 1 | |
| (SEQ ID NO: 25) | 5'-AAT TGG AGA GCA ATG GCT AGT GA-3' |
| HIV-1M primer 2 | |
| (SEQ ID NO: 26) | 5'-TGT GTA CAA TCT AAT TGC CAT A-3' |

F = FAM; Q = Dabcyl; the sequences which bind to the target nucleic acid are represented in bold The SH1BM14 probe is intended for the detection of the B genotype of HIV1-M, SH1BM17 for the C and D genotypes, and SH1BM18 for the E genotype.

The double-stranded probe according to the invention binds to the same target nucleic acid than SH1BM14. It also encompasses three mismatches with the corresponding target nucleic acid of the C genotype and two mismatches with the corresponding target nucleic acid of the D genotype.

The characteristics of the double-stranded probe are given in the following table:

| | Theo. Tm (° C.) | Theo. Δ Tm | Best Ta (° C.) |
|---|---|---|---|
| SEQ. ID NO: 23 + SEQ. ID NO: 24 | 50.4 | / | 50 |
| SEQ. ID NO: 23 + target | 57.7 | 7.3 | |
| SEQ. ID NO: 24 + target | 55.8 | 5.5 | |

The PCR mixes were as follows when used with the Molecular Beacon probes:

HIV RNA as indicated in the tables, SH1BM14 0.4 µM, SH1BM17 0.2 µM, SH1BM18 0.2 µM, HIV1-M primers 0.6 µM, 4 U HotStarTaq® Polymerase (QIAGEN, ref. 203207), 100 µM MgCl$_2$, d(ACGU)TP 400 µM, Quantitect® RT mix 0.5× (QIAGEN), 2.5% DMSO.

The PCR mixes were as follows when used with the double-stranded probe of the invention:

HIV RNA as indicated in the tables, double-stranded probe 0.1 µM, HIV1-M primers 0.15 µM, 4 U HotStarTaq® Polymerase (QIAGEN, ref. 203207), 100 µM MgCl$_2$, d(ACGU)TP 400 µM, Quantitect® RT mix 0.5× (QIAGEN), 2.5% DMSO.

Real time RT-PCR was conducted on a BioRad Chromo4 fluorescent thermocycler with the following thermoprofile:

```
30 min at 42° C. (reverse transcription)
15 min at 95° C. (HotStarTaq ® polymerase activation)
15 sec at 94° C.
20 sec at 55° C. (annealing)  ⎫
30 sec at 72° C.              ⎬  50 PCR cycles
                              ⎭
20° C.
```

Results

A. Samples Originating from the Supernatant of a Culture of Lymphoblastoid CEM Cells (HIV1-M B Subtype)

Reference Molecular Beacon (MB) probe SH1BM14 (Ta=55° C.):

| Initial number of target RNA copies/PCR | Ct | Mean Ct | SD | CV | Maximum Fluorescence |
|---|---|---|---|---|---|
| Negative control | 0 | 0.00 | 0.00 | | 0.004 |
| | 0 | | | | 0.004 |
| 2 | 37.9 | 38.88 | 1.38 | | 0.175 |
| | 39.85 | | | | 0.087 |
| | 0 | | | | 0.013 |
| 5 | 38.68 | 37.44 | 1.09 | 1.43 | 0.108 |
| | 36.6 | | | | 0.246 |
| | 37.05 | | | | 0.156 |
| 10 | 39.17 | 37.73 | 1.53 | −0.29 | 0.069 |
| | 36.13 | | | | 0.242 |
| | 37.89 | | | | 0.128 |
| 20 | 36.29 | 36.83 | 0.60 | 0.90 | 0.198 |
| | 36.73 | | | | 0.206 |
| | 37.48 | | | | 0.196 |
| 50 | 35.84 | 35.58 | 0.42 | 1.26 | 0.419 |
| | 35.8 | | | | 0.416 |
| | 35.09 | | | | 0.444 |
| 100 | 34.64 | 34.39 | 0.26 | 1.19 | 0.485 |
| | 34.4 | | | | 0.534 |
| | 34.12 | | | | 0.488 |
| $10^3$ | 31.21 | 31.26 | 0.06 | 3.13 | 0.740 |
| | 31.33 | | | | 0.660 |
| | 31.24 | | | | 0.724 |
| $10^4$ | 28.14 | 28.22 | 0.10 | 3.04 | 0.807 |
| | 28.33 | | | | 0.785 |
| | 28.2 | | | | 0.879 |
| $10^5$ | 24.52 | 24.45 | 0.06 | 3.77 | 0.905 |
| | 24.41 | | | | 0.949 |
| | 24.43 | | | | 0.950 |
| $10^6$ | 21.18 | 20.98 | 0.21 | 3.47 | 0.934 |
| | 21.01 | | | | 0.990 |
| | 20.76 | | | | 1.052 |

Correlation coefficient for Ct vs. log$_{10}$(Initial number of target RNA copies/PCR) = 0.98; Threshold value: 3.02 $10^{-2}$ Reference Molecular Beacon (MB) probes SH1BM14/17/18 (Ta=55° C.):

| Initial number of target RNA copies/PCR | Ct | Mean Ct | SD | CV | Maximum Fluorescence |
|---|---|---|---|---|---|
| Negative control | | 0.00 | 0.00 | | |
| | 0 | | | | 0.025 |
| | 0 | | | | 0.007 |
| 2 | 44.44 | 41.30 | 4.45 | | 0.047 |
| | 0 | | | | 0.009 |
| | 38.15 | | | | 0.241 |
| 5 | 39.55 | 39.09 | 0.90 | 2.20 | 0.090 |
| | 38.06 | | | | 0.189 |
| | 39.67 | | | | 0.086 |
| 10 | 37.6 | 37.97 | 0.68 | 1.12 | 0.221 |
| | 37.55 | | | | 0.199 |
| | 38.76 | | | | 0.100 |
| 20 | 36.38 | 36.44 | 0.24 | 1.53 | 0.268 |
| | 36.24 | | | | 0.314 |
| | 36.7 | | | | 0.320 |
| 50 | 36.4 | 36.37 | 0.04 | 0.07 | 0.317 |
| | 36.33 | | | | 0.394 |
| | 36.37 | | | | 0.358 |
| 100 | 35.04 | 35.10 | 0.35 | 1.27 | 0.460 |
| | 35.48 | | | | 0.437 |
| | 34.78 | | | | 0.482 |
| $10^3$ | 31.15 | 31.21 | 0.07 | 3.89 | 0.700 |
| | 31.28 | | | | 0.680 |
| | 31.19 | | | | 0.703 |
| $10^4$ | 27.82 | 27.98 | 0.14 | 3.23 | 0.810 |
| | 28.02 | | | | 0.748 |
| | 28.09 | | | | 0.850 |
| $10^5$ | 24.97 | 24.83 | 0.13 | 3.14 | 0.784 |
| | 24.81 | | | | 0.785 |
| | 24.72 | | | | 0.832 |
| $10^6$ | 21.21 | 21.16 | 0.05 | 3.67 | 0.842 |
| | 21.11 | | | | 0.858 |
| | 21.16 | | | | 0.867 |

Correlation coefficient for Ct vs. log$_{10}$(Initial number of target RNA copies/PCR) = 0.98; Threshold value: 3.02 $10^{-2}$ The same thermoprofile is used for the double-stranded probe compared to the Molecular Beacon probes, except the annealing temperature which was set at 50° C.

Double-stranded probe according to the invention (Ta=50° C.):

| Initial number of target RNA copies/PCR | Ct | Mean Ct | SD | CV | Maximum Fluorescence |
|---|---|---|---|---|---|
| Negative control | 0 | 0.00 | 0.00 | | 0.005 |
| | 0 | | | | 0.003 |
| | 0 | | | | 0.004 |
| 2 | 42 | 41.75 | 1.11 | | 0.161 |
| | 40.54 | | | | 0.633 |
| | 42.71 | | | | 0.702 |
| 5 | 38.18 | 40.96 | 2.67 | 0.79 | 1.034 |
| | 41.18 | | | | 0.866 |
| | 43.51 | | | | 0.150 |
| 10 | 41.03 | 40.44 | 0.83 | 0.52 | 0.877 |
| | 0 | | | | 0.011 |
| | 39.85 | | | | 0.974 |
| 20 | 36.39 | 37.60 | 1.16 | 2.84 | 1.106 |
| | 37.71 | | | | 1.089 |
| | 38.71 | | | | 0.872 |
| 50 | 37.69 | 37.20 | 0.44 | 0.40 | 0.988 |
| | 37.07 | | | | 1.239 |
| | 36.84 | | | | 1.005 |
| 100 | 34.94 | 35.36 | 0.62 | 1.84 | 1.260 |
| | 35.08 | | | | 1.211 |
| | 36.07 | | | | 1.038 |
| $10^3$ | 31.5 | 31.40 | 0.12 | 3.97 | 1.234 |
| | 31.27 | | | | 1.290 |
| | 31.42 | | | | 1.178 |
| $10^4$ | 27.76 | 27.77 | 0.16 | 3.63 | 1.157 |
| | 27.61 | | | | 1.252 |
| | 27.93 | | | | 1.238 |

-continued

| Initial number of target RNA copies/PCR | Ct | Mean Ct | SD | CV | Maximum Fluorescence |
|---|---|---|---|---|---|
| $10^5$ | 24.14 | 23.91 | 0.24 | 3.86 | 1.257 |
|  | 23.67 |  |  |  | 1.308 |
|  | 23.92 |  |  |  | 1.259 |
| $10^6$ | 20.62 | 20.45 | 0.15 | 3.46 | 1.196 |
|  | 20.42 |  |  |  | 1.224 |
|  | 20.32 |  |  |  | 1.186 |

Correlation coefficient for Ct vs. $\log_{10}$(Initial number of target RNA copies/PCR) = 0.98; Threshold value: $3.02 \cdot 10^{-2}$ The results are summarized in the following tables:
Reference Molecular Beacon (MB) probe SH1BM14 vs. double-stranded probe

| Initial number of target RNA copies/PCR | Ct MB/Ct DS | Fluorescence gain (%) |
|---|---|---|
| 2 | 1.09 | 444 |
| 5 | 1.07 | 302 |
| 10 | 1.09 | 324 |
| 20 | 1.02 | 411 |
| 50 | 1.05 | 153 |
| 100 | 1.03 | 133 |
| $10^3$ | 1.00 | 74 |
| $10^4$ | 0.98 | 48 |
| $10^5$ | 0.98 | 36 |
| $10^6$ | 0.97 | 21 |

Reference Molecular Beacon (MB) probes SH1BM14/17/18 vs. double-stranded probe

| Initial number of target RNA copies/PCR | Ct MB/Ct DS | Fluorescence gain (%) |
|---|---|---|
| 2 | 1.01 | 404 |
| 5 | 1.05 | 462 |
| 10 | 1.07 | 258 |
| 20 | 1.03 | 240 |
| 50 | 1.03 | 202 |
| 100 | 1.01 | 154 |
| $10^3$ | 1.01 | 78 |
| $10^4$ | 0.99 | 51 |
| $10^5$ | 0.96 | 59 |
| $10^6$ | 0.97 | 40 |

As can be seen from the foregoing tables the double-stranded probe according to the invention yields similar results than the reference Molecular Beacon probes as regards the detection threshold (2 copies per PCR), Ct values, linearity (correlation coefficients) and reproducibility (SD).

Besides it should be noted that a fluorescence gain of 194.6% on average is obtained as compared to the reference Molecular Beacon probes.

Figure 4A:
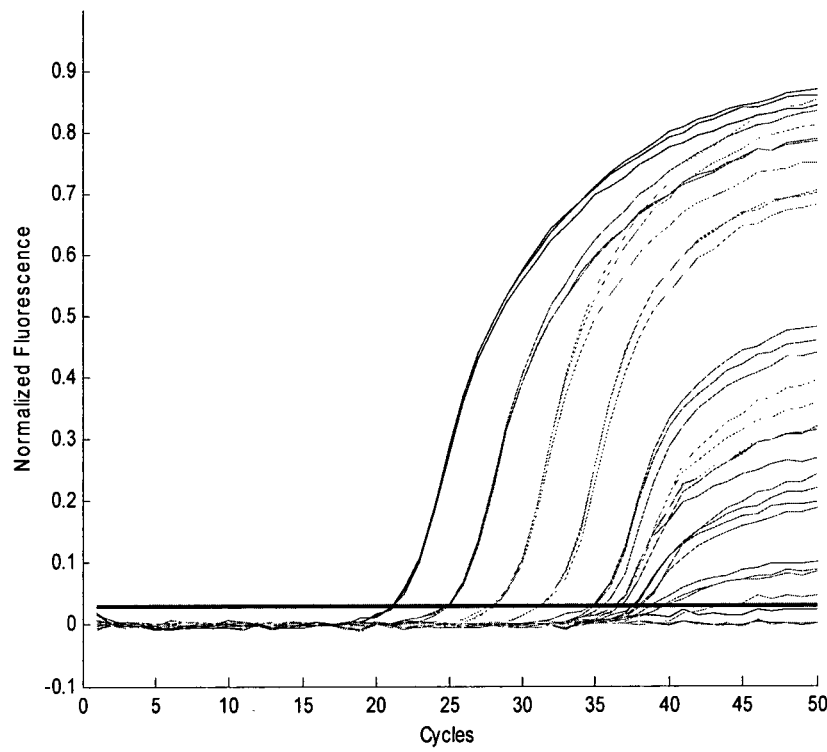
FIG. 4A and FIG. 4B respectively represent curves of normalized fluorescence vs. number of cycles in real-time RT-PCR assays for the detection of HIV-1M (as described in Example 7) in presence of a double-stranded probe according to the invention (FIG. 4B) or reference Molecular Beacon probes (FIG. 4A)
Figure 4B:
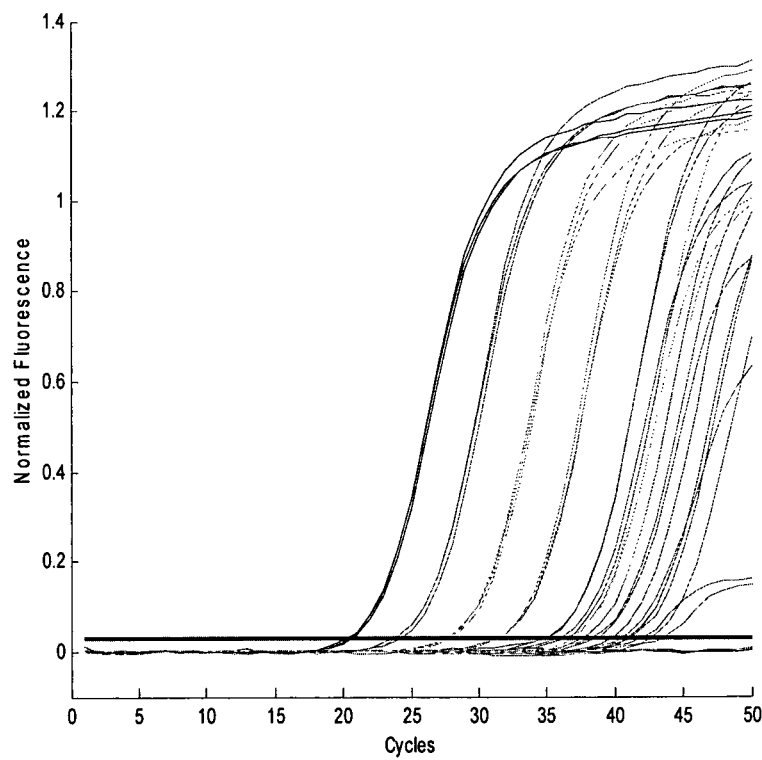

Furthermore the comparison of the Fluorescence vs. Number of cycles curves for the double-stranded probes (FIG. 4A) and the SH1BM14/17/18 Molecular Beacon probes (FIG. 4B) clearly shows that the curves obtained with the double-stranded probe have a more pronounced sigmoidicity and the curves are more regrouped, which enables a better discrimination between the negative controls (water) and assays with a low amount of target nucleic acid.

In addition, 4 times less probes and primers are needed when using the double-stranded probe of the invention than when using the SH1BM14/17/18 Molecular Beacon probes.

Upon varying the annealing temperature of the real-time RT-PCR between 48 and 55° C., the inventors showed that the double-stranded probes of the invention remained fully functional.

B. PRD201 Panel (HIV1-M Subtypes A, B, C, D, E, F, G and H)

Reference Molecular Beacon (MB) probe SH1BM14 (Ta=55° C.):

| Panel PRD201 | Ct | Mean Ctt | SD | Maximum Fluorescence |
|---|---|---|---|---|
| A | 35.75 | 35.74 | 0.02 | 0.362 |
|  | 35.72 |  |  | 0.380 |
| B | 32.22 | 32.15 | 0.11 | 0.628 |
|  | 32.07 |  |  | 0.584 |
| C | 0 | 0.00 | 0.00 | 0.025 |
|  | 0 |  |  | 0.029 |
| D | 35.57 | 36.16 | 0.83 | 0.069 |
|  | 36.74 |  |  | 0.054 |
| E | 39.51 | 39.51 |  | 0.041 |
|  | 0 |  |  | 0.032 |
| F | 31.49 | 31.36 | 0.18 | 0.785 |
|  | 31.23 |  |  | 0.784 |
| G | 32.2 | 31.96 | 0.35 | 0.939 |
|  | 31.71 |  |  | 0.867 |
| H | 31.03 | 30.90 | 0.18 | 1.067 |
|  | 30.77 |  |  | 1.024 |

Threshold value: $3.02 \cdot 10^{-2}$

Reference Molecular Beacon (MB) probe SH1BM14/17/18 (Ta=55° C.):

| Panel PRD201 | Ct | Mean Ct | SD | Maximum fluorescence |
|---|---|---|---|---|
| A | 35.89 | 36.28 | 0.54 | 0.338 |
|  | 36.66 |  |  | 0.271 |
| B | 31.32 | 31.67 | 0.49 | 0.654 |
|  | 32.02 |  |  | 0.611 |
| C | 35.91 | 36.13 | 0.31 | 0.181 |
|  | 36.35 |  |  | 0.195 |
| D | 33.52 | 33.61 | 0.13 | 0.177 |
|  | 33.7 |  |  | 0.168 |
| E | 33.92 | 34.10 | 0.25 | 0.313 |
|  | 34.28 |  |  | 0.275 |
| F | 30.75 | 30.88 | 0.18 | 0.661 |
|  | 31.01 |  |  | 0.673 |
| G | 33.07 | 33.09 | 0.02 | 0.590 |
|  | 33.1 |  |  | 0.568 |
| H | 30.97 | 30.84 | 0.19 | 0.800 |
|  | 30.7 |  |  | 0.785 |

Threshold value: $3.02 \cdot 10^{-2}$

Double-stranded probe according to the invention (Ta=50° C.):

| Panel PRD201 | Ct | Mean Ct | SD | Maximum Fluorence |
|---|---|---|---|---|
| A | 38.25 | 37.95 | 0.43 | 0.445 |
|  | 37.64 |  |  | 0.452 |
| B | 33 | 32.73 | 0.38 | 1.067 |
|  | 32.46 |  |  | 1.164 |
| C | 37.01 | 36.86 | 0.21 | 0.402 |
|  | 36.71 |  |  | 0.392 |
| D | 31.57 | 31.57 | 0.01 | 0.680 |
|  | 31.56 |  |  | 0.714 |
| E | 36.21 | 36.01 | 0.29 | 0.249 |
|  | 35.8 |  |  | 0.271 |
| F | 32.07 | 31.86 | 0.30 | 1.090 |
|  | 31.64 |  |  | 1.119 |
| G | 34.5 | 34.41 | 0.13 | 0.453 |
|  | 34.31 |  |  | 0.460 |
| H | 32.71 | 32.54 | 0.25 | 0.973 |
|  | 32.36 |  |  | 0.988 |

Threshold value: $3.02 \cdot 10^{-2}$

It should be noted that the double-stranded probe according to the invention enables the detection of all A to H genotypes, in particular subtypes C, D and E, which are either not detected by the SH1BM14 Molecular Beacon probe (subtype C), or detected with a high Ct value (subtype E) or yet detected with a very low fluorescence intensity slightly above the background (subtype D).

A fluorescence gain of 74.4% on average is observed for the majority of genotypes by using the double-stranded probe with respect to the three Molecular Beacon probes.

Furthermore, 4 times less probes and primers need to be used with the double-stranded probe according to the invention by comparison with the three molecular Beacon probes.

Example 8

Multiplex Detection of HIV1-M and HIV1-O genomes
The following additional probes were used:

| Probe/Primer sequences | |
|---|---|
| Molecular Beacon probe | |
| HIV-1O (SEQ ID NO: 27) | 5'F-CGCGCA AGT CTA CCT GAC CAT GAA TTG CTT CCC CTT TTA TGCGCG-Q3' |
| Double-stranded probe HIV-1O | |
| (SEQ ID NO: 28) | 5'F-TTTT CTG ACC ATG AAT TGC TTC CCCT-Q3' |
| (SEQ ID NO: 29) | 3'Q-GATG GAC TGG TAC TTA ACG AAG TTTT-F5' |
| HIV-1O primer 1 | |
| (SEQ ID NO: 25) | 5'-AAT TGG AGA GCA ATG GCT AGT GA-3' |
| HIV-1O primer 2 | |
| (SEQ ID NO: 30) | 5'-TGT GTA CAA TCT ATT TGC CAT A-3' |

F = FAM; Q = Dabcyl; the sequences which bind to the target nucleic acid are represented in bold The characteristics of the double-stranded probe are given in the following table:

|  | Theo. Tm (° C.) | Theo. Δ Tm | Best Ta (° C.) |
|---|---|---|---|
| SEQ. ID NO: 28 + SEQ. ID NO: 29 | 46.0 | / | 50 |
| SEQ. ID NO: 28 + target | 53.4 | 7.4 | |
| SEQ. ID NO: 29 + target | 53.4 | 7.4 | |

The PCR mix was as follows when used with the double-stranded probe of the invention:
Double-stranded probe HIV1-M 0.1 μM, double-stranded probe HIV1-O 0.1 μM, HIV1-M/O primer SEQ. ID No 25 0.15 μM, HIV1-M primer SEQ. ID No 26 0.075 μM, HIV1-O primer SEQ. ID No 30 0.15 μM, 4 U HotStarTaq® Polymerase (QIAGEN, ref. 203207), 100 μM MgCl$_2$, d(ACGU)TP 400 μM, Quantitect® RT mix 1× (QIAGEN), 2.5% DMSO.

The results obtained with the probes for the detection of HIV1-M mixed to the HIV1-O probes described above using samples originating from the supernatant of a culture of lymphoblastoid CEM cells are presented in the following table (Ta=50° C.):

| Initial number of target RNA copies/PCR | Ct | Mean Ct | SD | CV | Maximum Fluorescence |
|---|---|---|---|---|---|
| Negative control | 0 | | | | 0.016 |
| | 0 | | | | 0.018 |
| | 0 | | | | 0.017 |
| 10 | 40.05 | 40.96 | 0.85 | | 0.556 |
| | 41.11 | | | | 0.653 |
| | 41.73 | | | | 0.654 |
| 20 | 40.33 | 40.05 | 0.25 | 0.92 | 0.693 |
| | 39.9 | | | | 0.707 |
| | 39.91 | | | | 0.691 |
| 50 | 38.61 | 38.81 | 0.28 | 1.24 | 0.726 |
| | 40.94 | | | | 0.629 |
| | 39.01 | | | | 0.776 |
| 100 | 37.51 | 37.48 | 0.34 | 1.33 | 0.690 |
| | 37.8 | | | | 0.654 |
| | 37.12 | | | | 0.773 |
| $10^3$ | 34.2 | 34.24 | 0.07 | 3.24 | 0.774 |
| | 34.32 | | | | 0.763 |
| | 34.19 | | | | 0.827 |
| $10^4$ | 30.13 | 29.96 | 0.34 | 4.28 | 0.783 |
| | 29.57 | | | | 0.808 |
| | 30.18 | | | | 0.804 |

Correlation coefficient for Ct vs. log$_{10}$(Initial number of target RNA copies/PCR) = 0.99; Threshold value = 2.73 10$^{-2}$ Good threshold of detection, Cts, linearity and reproducibility could thus be evidenced.

The fluorescence are well within working standards.

The normalized fluorescence vs. number of cycle curves are sigmoid-like and are regrouped over the whole range of initial DNA concentrations, thus enabling a good discrimination between the water negative controls and samples with low DNA copies, as evidenced for HIV1-M simplex detection.

As such, the inventors showed that small quantities (0.1 μM) of the double-stranded probe according to the invention were also effective in duplex assays.

Furthermore, the results obtained with the probes for the detection of HIV1-O mixed to those described in Example 7 on the PRD201 panel (HIV-1M) and on the BBI 301 panel (HIV1-O) are presented in the following two tables: (Ta=50° C.):

| PRD201 HIV-1M | Ct | Mean Ct | SD | Maximum Fluorescence |
|---|---|---|---|---|
| Negative control | 0 | | | 0.028 |
| | 0 | | | 0.032 |
| | 0 | | | 0.036 |
| A | 40.3 | 40.46 | 0.23 | 0.291 |
| | 40.62 | | | 0.330 |
| B | 35.12 | 35.53 | 0.58 | 0.887 |
| | 35.94 | | | 0.777 |
| C | 41.36 | 41.11 | 0.36 | 0.249 |
| | 40.85 | | | 0.234 |
| D | 35.37 | 35.36 | 0.01 | 0.444 |
| | 35.35 | | | 0.472 |
| E | 40.98 | 40.70 | 0.40 | 0.128 |
| | 40.42 | | | 0.134 |
| F | 34.74 | 34.76 | 0.02 | 0.835 |
| | 34.77 | | | 0.812 |
| G | 40.88 | 40.66 | 0.32 | 0.227 |
| | 40.43 | | | 0.255 |

| PRD201 HIV-1M | Ct | Mean Ct | SD | Maximum Fluorescence |
|---|---|---|---|---|
| H | 36.42 | 36.27 | 0.21 | 0.688 |
|   | 36.12 |   |   | 0.752 |

Threshold value = 2.73 $10^{-2}$

| BBI 301 HIV-1O | Ct | Mean Ct | SD | Maximum Fluorescence |
|---|---|---|---|---|
| 301-1 | 40.89 | 40.95 | 0.08 | 0.108 |
|   | 41.01 |   |   | 0.103 |
| 301-2 | 36.05 | 36.21 | 0.23 | 1.650 |
|   | 36.37 |   |   | 1.711 |
| 301-3 | 40.49 | 39.24 | 1.77 | 0.708 |
|   | 37.98 |   |   | 0.786 |
| 301-4 | 37.27 | 37.58 | 0.44 | 1.162 |
|   | 37.89 |   |   | 1.038 |

Threshold value = 2.73 $10^{-2}$

The double-stranded probes according to the invention, can detect of HIV1-M genotypes (from A to H, in particular the C, D and E subtypes which are not detected by the SH1BM14 Molecular Beacon probe alone) and all the genotypes of the HIV1-O panel in a duplex assay.

Example 9

Multiplex Assay HBV Zone A (FAM/Atto647N)—Quantification

A multiplex assay combining (i) the detection of the A zone of the HBV genome and of an internal control (IC) and (ii) the quantification of HBV was set out using the Atto647N dye instead of the Atto532 dye for IC detection, using the probes and primers of Examples 4 and 5 (designated "System 1" hereafter), and an alternative double-stranded probe according to the invention (designated "System 2" hereafter).

Briefly, the following template DNA, probe and primer concentrations were used in the otherwise similar mixes of Example 2:

IC DNA 300 copies per PCR,
HBV DNA 100-$10^6$ copies per PCR,
BV primers 0.6 μM,
IC primers 0.3 μM;
Molecular Beacon IC probe (0.2 μM), System 1 double-stranded IC probe (0.1 μM of each strand), or System 2 double-stranded IC probe (0.05 μM of each strand);
Molecular Beacon HBV probe (0.6 μM), System 1 double-stranded HBV probe (0.2 μM of each strand), or System 2 double-stranded HBV probe (0.05 μM of each strand);
HotStarTaq® Polymerase (QIAGEN ref 203205) 2.5 U, MgCl$_2$ 6 mM, d(ACGU)TP 200 μM, dTTP 100 μM, 0.25 U UDG, PVP 0.3%, glycerol 5%.

The thermoprofile used is the same as for Example 7.
The following double-stranded probes for the System 2 were used:

| Probe sequences-System2-HBV |
|---|
| Molecular Beacon probe |
| (SEQ ID NO: 8)   5' F-CGGCA GGA GTC CGC GTA AAG AGA GGT G TGCCG-Q 3' |

| Probe sequences-System2-HBV |
|---|
| Double-stranded probe |
| (SEQ ID NO: 67)   5' F-TTTT CTC TCT TTA CGC GGA CTC CCCG-Q 3' |
| (SEQ ID NO: 68)   3' Q-CGTG GAG AGA AAT GCG CCT GAG TTTT-F 5' |

F = FAM; Q = Dabcyl; the sequences which bind to the target nucleic acid are represented in bold

| Probe sequences-System2-IC |
|---|
| Molecular Beacon probe |
| (SEQ ID NO: 13)   5' F-TGCTGC GT CCT CCG CCG CCA CCG CTT GG GCAGCA-Q 3' |
| Double-stranded probe |
| (SEQ ID NO: 69)   5' F-TTTT AAG CGG TGG CGG CGG A GGAC-Q 3' |
| (SEQ ID NO: 70)   3' Q-GCGG TTC GCC ACC GCC GCC T TTTT-F 5' |

F = Atto647N; Q = Dabcyl; the sequences which bind to the target nucleic acid are represented in bold Detection of FAM Fluorescence (HBV DNA Detection):
Reference Molecular Beacon (MB) probe (Ta=55° C.):

| Initial number of target DNA copies/PCR | Ct | Mean Ct | Maximum Fluorescence |
|---|---|---|---|
| 100 | 36.09 | 36.1 | 0.494 |
|   | 36.01 |   | 0.484 |
| 1000 | 32.77 | 32.5 | 0.601 |
|   | 32.15 |   | 0.699 |
| $10^4$ | 29.12 | 29.1 | 0.646 |
|   | 29.07 |   | 0.731 |
| $10^5$ | 25.86 | 25.5 | 0.716 |
|   | 25.14 |   | 0.750 |
| $10^6$ | 21.27 | 21.4 | 0.778 |
|   | 21.51 |   | 0.760 |

Correlation coefficient for Ct vs. log10(Initial number of target DNA copies/PCR) = 0.997; Threshold value: 1.5 $10^{-2}$ Double-stranded (DS) probe (System 1) (Ta=55° C.):

| Initial number of target DNA copies/PCR | Ct | Mean Ct | Maximum Fluorescence |
|---|---|---|---|
| 100 | 36.42 | 36.3 | 0.534 |
|   | 36.24 |   | 0.518 |
| 1000 | 32.18 | 32.5 | 0.672 |
|   | 32.77 |   | 0.741 |
| $10^4$ | 29.04 | 29.2 | 0.921 |
|   | 29.45 |   | 0.802 |
| $10^5$ | 25.56 | 25.9 | 0.923 |
|   | 26.25 |   | 0.845 |
| $10^6$ | 22.61 | 21.9 | 0.873 |
|   | 21.12 |   | 0.973 |

Correlation coefficient for Ct vs. log10(Initial number of target DNA copies/PCR) = 0.992; Threshold value: 1.8 $10^{-2}$ Double-stranded (DS) probe (System 2) (Ta=55° C.):

| Initial number of target DNA copies/PCR | Ct | Mean Ct | Maximum Fluorescence |
|---|---|---|---|
| 100 | 37.00 | 37.1 | 0.271 |
|  | 37.23 |  | 0.335 |
| 1000 | 33.22 | 32.7 | 0.427 |
|  | 32.16 |  | 0.495 |
| $10^4$ | 29.85 | 29.8 | 0.488 |
|  | 29.84 |  | 0.447 |
| $10^5$ | 26.82 | 26.6 | 0.545 |
|  | 26.42 |  | 0.583 |
| $10^6$ | 22.47 | 22.5 | 0.585 |
|  | 22.55 |  | 0.581 |

Correlation coefficient for Ct vs. log10(Initial number of target DNA copies/PCR) = 0.993; Threshold value: $8\ 10^{-3}$ The results are summarized for the System 1 in the following table:

| Initial number of target DNA copies/PCR | Ct MB/Ct DS | Fluorescence gain (%) |
|---|---|---|
| 100 | 0.99 | 7.5 |
| 1000 | 1.00 | 8.7 |
| $10^4$ | 0.99 | 25.1 |
| $10^5$ | 0.98 | 20.6 |
| $10^6$ | 0.98 | 20.0 |
|  |  | Mean: 16.4 |

Fluorescence gain is calculated with the following formula: [(Max. fluorescence DS − Max. fluorescence MB)/Max. fluorescence MB] × 100

The results are summarized for the System 2 in the following table:

| Initial number of target DNA copies/PCR | Ct MB/Ct DS | Fluorescence gain (%) |
|---|---|---|
| 100 | 0.97 | −38.0 |
| 1000 | 0.99 | −29.1 |
| $10^4$ | 0.98 | −32.1 |
| $10^5$ | 0.96 | −23.0 |
| $10^6$ | 0.95 | −24.2 |
|  |  | Mean: −29.3 |

Fluorescence gain is calculated with the following formula: [(Max. fluorescence DS − Max. fluorescence MB)/Max. fluorescence MB] × 100

Detection of Atto647N Fluorescence (IC DNA Detection):

As expected this detection yielded essentially constant results and equivalent for both probe systems.

|  | Mean Ct | Maximum fluorescence | CV |
|---|---|---|---|
| Reference Molecular Beacon (MB) probe | 31.83 | 0.585 | 0.19 |
| Double-stranded (DS) probe (System 1) | 33.10 | 0.554 | 0.36 |
| Double-stranded (DS) probe (System 2) | 31.41 | 0.502 | 0.40 |

Quantification of HBV DNA

| | Sample 1: 40 copies/PCR 20-80 copies/PCR | Sample 2: 4000 copies/PCR 2000-8000 copies/PCR | Sample 3: $4.10^5$ copies/PCR $2\ 10^5$-$8\ 10^5$ copies/PCR | $R^2$ |
|---|---|---|---|---|
| Reference Molecular Beacon (MB) probe | 154 | 7804 | $3.09\ 10^5$ | 0.997 |
| Double-stranded (DS) probe (System 1) | 105 | 7958 | $3.57\ 10^5$ | 0.992 |
| Double-stranded (DS) probe (System 2) | 78 | 7829 | $4.14\ 10^5$ | 0.992 |

The Ct values measured using two different systems of double-stranded probe according to the invention are similar to those measured with a reference Molecular Beacon probe, the sensitivity is similar using both probes, and the linear regression of Ct with respect to the initial number of target DNA copies for the two systems of double-stranded probe presents a high correlation coefficient ($R^2$=0.992), in line with what can be observed for the reference Molecular Beacon probe.

As previously observed, the results could be achieved with lower concentrations of the double-stranded probes as compared to the Molecular Beacon probes.

Furthermore, the results obtained for this multiplex assay indicate that double-stranded probes according to the invention are fully functional with a fluorescent dye having a high emission wavelength such as Atto647N.

Finally, the results obtained for this multiplex assay indicate that double-stranded probes according to the invention are fully functional for the quantification of HBV DNA.

Example 10

Simplex Assay HIV (FAM)—Alternative Configuration 5'FAM/3'FAM and 5'Dabcyl/3'Dabcyl A simplex assay was set out using two alternative configurations of the double-stranded probe according to the invention (the two fluorophores on a same strand and the two quenchers on the other same strand, and vice versa: System A and System B) for the detection of various genotypes of HIV-1M detection, using the probes and primers of Examples 7.

Briefly, the following template RNA, probe and primer concentrations were used in the otherwise similar mixes of Example 7:

HIV RNA as indicated in the tables;
Primers 0.15 μM;
Double-stranded HIV probe 0.1 μM of each strand;
HotStarTaq® (QIAGEN ref 203207) 4 U, MgCl$_2$ 0.1 mM, d(ACGU)TP 100 mM, 2.5% DMSO;
Quantitect® RT Mix 1× (Qiagen).

The thermoprofile used is the same as for Example 7, except for the annealing temperature which was set at 48° C.

The following double-stranded probes for the systems A and B were used:

| Probe sequence-Reference-HIV-1M | | |
|---|---|---|
| (SEQ ID NO: 23) | 5'F-TTTT | CCA GCT GTG ATA AAT G TCAG-Q3' |
| (SEQ ID NO: 24) | 3'Q-CATC GGT CGA CAC TAT TTA C TTTT-F5' | |

F = FAM; Q = Dabcyl; the sequences which bind to the target nucleic acid are represented in bold

| Probe sequence-System A-HIV-1M | |
|---|---|
| SEQ ID NO: 23 | 5'F-TTTT CCA GCT GTG ATA AAT G TCAG-F 3' |
| SEQ ID NO: 24 | 3'Q-CATC GGT CGA CAC TAT TTA C TTTT-Q 5' |

F = FAM; Q = Dabcyl; the sequences which bind to the target nucleic acid are represented in bold

| Probe sequence-System B-HIV-1M | |
|---|---|
| SEQ ID NO: 23 | 5'Q-TTTT CCA GCT GTG ATA AAT G TCAG-Q 3' |
| SEQ ID NO: 24 | 3'F-CATC GGT CGA CAC TAT TTA C TTTT-F 5' |

F = FAM; Q = Dabcyl; the sequences which bind to the target nucleic acid are represented in bold Results A. Samples Originating from the Supernatant of a Culture of Lymphoblastoid CEM cells (HIV-1 M B subtype)

Reference Double-Stranded (DS) probe:

| Initial number of target RNA copies/PCR | Ct | Mean Ct | SD | CV | Maximum Fluorescence |
|---|---|---|---|---|---|
| Negative control | 0 | 0.00 | 0.00 | | 0.021 |
| | 0 | | | | 0.016 |
| | 0 | | | | 0.011 |
| 10 | 38.17 | 38.42 | 0.85 | | 1.117 |
| | 39.37 | | | | 1.064 |
| | 37.72 | | | | 1.195 |
| 20 | 36.38 | 37.14 | 0.72 | 1.28 | 1.216 |
| | 37.8 | | | | 1.005 |
| | 37.25 | | | | 1.206 |
| 50 | 35.23 | 36.10 | 0.76 | 1.04 | 1.194 |
| | 36.53 | | | | 0.995 |
| | 36.55 | | | | 0.968 |
| 100 | 34.91 | 34.88 | 0.46 | 1.22 | 1.013 |
| | 34.41 | | | | 1.052 |
| | 35.33 | | | | 1.139 |
| $10^3$ | 31.52 | 31.26 | 0.28 | 3.62 | 1.141 |
| | 31.31 | | | | 1.134 |
| | 30.96 | | | | 1.128 |
| $10^4$ | 26.9 | 26.92 | 0.19 | 4.34 | 1.084 |
| | 27.12 | | | | 1.239 |
| | 26.75 | | | | 1.255 |
| $10^5$ | 23.48 | 23.49 | 0.04 | 3.43 | 1.249 |
| | 23.46 | | | | 1.288 |
| | 23.54 | | | | 1.311 |
| $10^6$ | 19.86 | 19.80 | 0.06 | 3.69 | 1.291 |
| | 19.8 | | | | 1.286 |
| | 19.74 | | | | 1.230 |

Correlation coefficient for Ct vs. $\log_{10}$(Initial number of target RNA copies/PCR) = 0.99; Threshold value: $2.6 \cdot 10^{-2}$ System A double-stranded (DS) probe:

| Initial number of target RNA copies/PCR | Ct | Mean Ct | SD | CV | Maximum Fluorescence |
|---|---|---|---|---|---|
| Negative control | 0 | 0.00 | 0.00 | | 0.017 |
| | 0 | | | | 0.020 |
| | 0 | | | | 0.018 |
| 10 | 43.19 | 38.00 | 0.64 | | 0.405 |
| | 38.45 | | | | 0.647 |
| | 37.55 | | | | 0.696 |
| 20 | 39 | 38.08 | 0.81 | −0.08 | 0.679 |
| | 37.46 | | | | 0.689 |
| | 37.78 | | | | 0.640 |
| 50 | 36.57 | 36.31 | 0.42 | 1.77 | 0.653 |
| | 36.53 | | | | 0.660 |
| | 35.83 | | | | 0.564 |
| 100 | 34.84 | 34.87 | 0.27 | 1.44 | 0.701 |
| | 34.62 | | | | 0.747 |
| | 35.16 | | | | 0.727 |
| $10^3$ | 32.17 | 31.81 | 0.36 | 3.07 | 0.739 |
| | 31.46 | | | | 0.723 |
| | 31.79 | | | | 0.732 |
| $10^4$ | 27.72 | 27.40 | 0.29 | 4.41 | 0.706 |
| | 27.17 | | | | 0.760 |
| | 27.3 | | | | 0.794 |
| $10^5$ | 24.12 | 24.36 | 0.22 | 3.03 | 0.789 |
| | 24.42 | | | | 0.795 |
| | 24.55 | | | | 0.753 |
| $10^6$ | 20.46 | 20.63 | 0.14 | 3.74 | 0.823 |
| | 20.72 | | | | 0.771 |
| | 20.7 | | | | 0.732 |

Correlation coefficient for Ct vs. $\log_{10}$(Initial number of target RNA copies/PCR) = 0.99; Threshold value: $2.6 \cdot 10^{-2}$ System B double-stranded (DS) probe:

| Initial number of target RNA copies/PCR | Ct | Mean Ct | SD | CV | Maximum Fluorescence |
|---|---|---|---|---|---|
| Negative control | 0 | 0.00 | 0.00 | | 0.032 |
| | 0 | | | | 0.029 |
| | 0 | | | | 0.032 |
| 10 | 37.14 | 38.92 | 0.62 | | 0.777 |
| | 39.36 | | | | 0.693 |
| | 38.48 | | | | 0.687 |
| 20 | 37.68 | 37.29 | 0.55 | 1.63 | 0.771 |
| | 36.9 | | | | 0.789 |
| | 38.59 | | | | 0.609 |
| 50 | 35.63 | 35.76 | 0.39 | 1.53 | 0.773 |
| | 35.45 | | | | 0.718 |
| | 36.2 | | | | 0.750 |
| 100 | 34.87 | 34.82 | 0.37 | 0.94 | 0.827 |
| | 34.43 | | | | 0.810 |
| | 35.16 | | | | 0.833 |
| $10^3$ | 30.78 | 30.99 | 0.20 | 3.83 | 0.960 |
| | 31.02 | | | | 0.913 |
| | 31.17 | | | | 0.949 |
| $10^4$ | 27.01 | 27.31 | 0.30 | 3.68 | 0.894 |
| | 27.6 | | | | 0.835 |
| | 27.33 | | | | 0.874 |
| $10^5$ | 24.08 | 24.08 | 0.05 | 3.23 | 0.883 |
| | 24.03 | | | | 0.902 |
| | 24.13 | | | | 0.908 |
| $10^6$ | 20.78 | 20.65 | 0.11 | 3.43 | 0.862 |
| | 20.57 | | | | 0.877 |
| | 20.6 | | | | 0.879 |

Correlation coefficient for Ct vs. $\log_{10}$(Initial number of target RNA copies/PCR) = 0.99; Threshold value: $2.6 \cdot 10^{-2}$ As can be seen from the foregoing tables, the double-stranded probes with the alternative configuration (the two dyes on the same strand and the two quenchers on the other same strand) yield similar results than the reference double-stranded probes as regards the detection threshold (10 copies per PCR), Ct values, and reproducibility (SD).

B. PRD201 Panel (HIV1-M Subtypes A, B, C, D, E, F, G and H)

Reference Double-Stranded (DS) probe:

| Panel PRD201 | Ct | Mean Ct | SD | Maximum Fluorescence |
|---|---|---|---|---|
| A | 37.07 | 37.17 | 0.14 | 0.649 |
|   | 37.27 |   |   | 0.664 |
| B | 32.11 | 32.08 | 0.04 | 1.211 |
|   | 32.05 |   |   | 1.265 |
| C | 36.28 | 36.44 | 0.22 | 0.526 |
|   | 36.59 |   |   | 0.627 |
| D | 31.93 | 31.89 | 0.06 | 0.734 |
|   | 31.84 |   |   | 0.760 |
| E | 35.61 | 35.65 | 0.06 | 0.418 |
|   | 35.69 |   |   | 0.406 |
| F | 31.34 | 31.21 | 0.19 | 1.134 |
|   | 31.07 |   |   | 1.120 |
| G | 35.01 | 35.12 | 0.16 | 0.515 |
|   | 35.23 |   |   | 0.493 |
| H | 32.96 | 32.86 | 0.14 | 0.960 |
|   | 32.76 |   |   | 0.980 |

Threshold value: $3.02 \cdot 10^{-2}$

System A double-stranded (DS) probe:

| Panel PRD201 | Ct | Mean Ct | SD | Maximum Fluorescence |
|---|---|---|---|---|
| A | 36.84 | 36.90 | 0.08 | 0.468 |
|   | 36.95 |   |   | 0.463 |
| B | 32.5 | 32.37 | 0.18 | 0.838 |
|   | 32.24 |   |   | 0.850 |
| C | 36.8 | 36.64 | 0.23 | 0.343 |
|   | 36.47 |   |   | 0.351 |
| D | 31.5 | 31.49 | 0.01 | 0.532 |
|   | 31.48 |   |   | 0.549 |
| E | 34.88 | 34.95 | 0.10 | 0.321 |
|   | 35.02 |   |   | 0.312 |
| F | 31.11 | 31.00 | 0.16 | 0.896 |
|   | 30.88 |   |   | 0.864 |
| G | 34.49 | 34.38 | 0.16 | 0.419 |
|   | 34.26 |   |   | 0.423 |
| H | 32.65 | 32.67 | 0.03 | 0.785 |
|   | 32.69 |   |   | 0.744 |

Threshold value: $2.6 \cdot 10^{-2}$

System B double-stranded (DS) probe:

| Panel PRD201 | Ct | Mean Ct | SD | Maximum Fluorescence |
|---|---|---|---|---|
| A | 36.74 | 37.42 | 0.95 | 0.555 |
|   | 38.09 |   |   | 0.533 |
| B | 32.37 | 32.19 | 0.26 | 0.927 |
|   | 32 |   |   | 0.963 |
| C | 36.38 | 36.43 | 0.07 | 0.489 |
|   | 36.48 |   |   | 0.431 |
| D | 31.37 | 31.73 | 0.50 | 0.619 |
|   | 32.08 |   |   | 0.605 |
| E | 36.04 | 35.45 | 0.84 | 0.334 |
|   | 34.85 |   |   | 0.353 |
| F | 31.38 | 31.08 | 0.43 | 0.974 |
|   | 30.77 |   |   | 0.913 |
| G | 34.63 | 34.75 | 0.16 | 0.443 |
|   | 34.86 |   |   | 0.477 |
| H | 32.29 | 32.29 | 0.00 | 0.872 |
|   | 32.29 |   |   | 0.833 |

Threshold value: $2.6 \cdot 10^{-2}$

All A to H genotypes can be detected by the double-stranded probes according to the invention, irrespective of the fluorophore/quencher configuration.

Example 11

Detection of *Salmonella typhi*

Double-stranded probes according to the invention were further tested in a real-time Polymerase Chain Reaction (PCR) simplex assay designed for the detection of *Salmonella typhi* (fragment of 155 nucleotides spanning nucleotides 1501 to 1655 of the iagA gene, NCBI CoreNucleotide reference X80892) compared to a reference Molecular Beacon probe.

Materials and Methods

A DNA plasmid including the *Salmonella typhi* targeted sequence (pUC18 plasmid including a HindIII-BamHI fragment of 619 base pairs from the iagA gene (positions 1114 to 1732 from X80892)) was extracted using classical plasmid preparation kits, according to the manufacturer's instructions. The DNA plasmid was diluted in water before use.

The following probes and primers were used:

| Probe/Primer sequences for *Salmonella* detection | |
|---|---|
| Molecular Beacon probe | |
| (SEQ ID NO: 71) | $^5{'}$F-CGCGAC TGT CAG AAT AGT GAG CGT GCC TTA C GTCGCG-Q$^{3'}$ |
| Double-stranded probe | |
| (SEQ ID NO: 72) | $^5{'}$F-TTT G AAT AGT GAG CGT GCC T TACCG-Q$^{3'}$ |
| (SEQ ID NO: 73) | $^3{'}$Q-ACAGT C TTA TCA CTC GCA CGG A TTT-F$^{5'}$ |
| Primer | |
| (SEQ ID NO: 74) | 5'-CAC GCA GGA AAT AAC AGG ACT T-3' |
| Primer | |
| (SEQ ID NO: 75) | 5'-GGG CAA CCA GCA CTA AC-3' |

F = FAM; Q = Dabcyl; the sequences which bind to the target nucleic acid are represented in bold The PCR mixes were as follows:
Plasmid DNA: 0-20,000 copies/PCR;
*Salmonella* primers 0.5 µM;
Molecular Beacon *Salmonella* probe 0.2 µM or double-stranded *Salmonella* probe 0.1 µM of each strand;
Polymerase (Fast Start Taq DNA polymerase (Roche) 3 U/reaction, HotStarTaq® Plus (Qiagen) 2.5 U/reaction, NovaTaq™ Hot Start (Novagen) 2 U/reaction, Dynazyme™ II DNA polymerase (Finnzymes) 3 U/reaction, Taq DNA polymerase (Roche) 3 U/reaction);
$MgCl_2$ 4 mM; d(ACGT)TP 100 µM.

Real time PCR was conducted on a BioRad Chromo4 fluorescent thermocycler with the following thermoprofile:

10 min at 95° C. (HotStarTaq ® polymerase activation) or 2 min at 95° C. (unmodified polymerases)
15 sec at 95° C.
20 sec at 55° C. (annealing) ⎫
30 sec at 72° C.          ⎬ 50 PCR cycles
20° C.                    ⎭

Results
Detection of FAM Fluorescence (*Salmonella* DNA Detection):

Hot Start Taq polymerases

| Initial number of target DNA | 2,5U Qiagen + | | | | 3U FastStart | | | |
|---|---|---|---|---|---|---|---|---|
| | Molecular Beacon probes | | Double-Stranded probes | | Molecular Beacon probes | | Double-Stranded probes | |
| copies/PCR | Ct FAM | Mean Ct | Ct FAM | Mean Ct | Ct FAM | Mean Ct | Ct FAM | Mean Ct |
| Negative control | N/A N/A | N/A | N/A N/A | N/A | N/A N/A | N/A | N/A N/A | N/A |
| 20 | 47.67 41.47 | 44.57 | 37.55 39.00 | 38.28 | 41.35 43.27 | 42.31 | 38.07 37.54 | 37.81 |
| 200 | 37.85 38.63 | 38.24 | 35.36 35.06 | 35.21 | 38.27 38.20 | 38.24 | 35.12 34.95 | 35.04 |
| $2\ 10^3$ | 35.12 34.92 | 35.02 | 31.32 31.25 | 31.29 | 34.92 35.30 | 35.11 | 31.31 31.36 | 31.34 |
| $2\ 10^4$ | 31.57 31.46 | 31.52 | 27.92 28.06 | 27.99 | 31.70 31.59 | 31.65 | 27.82 27.66 | 27.74 |
| Range of fluorescence at the maximum level | 0.3 up to 1.15 | | 1.65 up to 2.5 | | 0.2 up to 0.6 | | 0.8 up tp 1.35 | |
| Threshold value | 0.25 | | 0.25 | | 0.10 | | 0.10 | |

| Initial number of target DNA | 2U Novagen | | | |
|---|---|---|---|---|
| | Molecular Beacon probes | | Double-Stranded probes | |
| copies/PCR | Ct FAM | Mean Ct | Ct FAM | Mean Ct |
| Negative control | N/A N/A | N/A | N/A N/A | N/A |
| 20 | 42.13 N/A | 42.13 | 44.54 N/A | 44.54 |
| 200 | 38.06 38.61 | 38.34 | 38.75 38.09 | 38.42 |
| $2\ 10^3$ | 34.75 34.84 | 34.80 | 35.48 36.02 | 35.75 |
| $2\ 10^4$ | 31.38 31.43 | 31.41 | 32.34 32.33 | 32.34 |
| Range of fluorescence at the maximum level | 0.3 upt to 0.6 | | 0.5 up tp 1.2 | |
| Threshold value | 0.10 | | 0.10 | |

Other Polymerases

| Initial number of target DNA | 3U Dynazyme | | | | 3U Roche | | | |
|---|---|---|---|---|---|---|---|---|
| | Molecular Beacon probes | | Double-Stranded probes | | Molecular Beacon probes | | Double-Stranded probes | |
| copies/PCR | Ct FAM | Mean Ct | Ct FAM | Mean Ct | Ct FAM | Mean Ct | Ct FAM | Mean Ct |
| Negative control | N/A N/A | N/A | N/A N/A | N/A | N/A N/A | N/A | N/A N/A | N/A |
| 20 | 38.44 38.86 | 38.65 | 37.34 38.76 | 38.05 | 41.99 43.5 | 42.75 | 38.97 37.88 | 38.43 |
| 200 | 37.29 38.25 | 37.77 | 34.88 34.15 | 34.52 | 38.89 39.32 | 39.11 | 35.22 35.7 | 35.46 |
| $2\ 10^3$ | 33.87 34.12 | 34.00 | 31.45 31.21 | 31.33 | 35.93 35.77 | 35.85 | 32.05 32.03 | 32.04 |
| $2\ 10^4$ | 30.9 30.89 | 30.90 | 27.89 27.97 | 27.93 | 32.48 32.31 | 32.40 | 28.54 28.28 | 28.41 |
| Range of fluorescence at the maximum level | 0.25 up to 0.7 | | 1 up to 2.1 | | 0.3 up to 0.65 | | 0.9 up to 1.75 | |
| Threshold value | 0.18 | | 0.18 | | 0.18 | | 0.18 | |

Overall, results obtained for the simplex assay indicate that double-stranded probes according to the invention are fully functional for detection of *Salmonella typhi* DNA.

The Ct values measured using the double-stranded probe according to the invention are similar or, advantageously, lower to those measured with the reference Molecular Beacon probe.

The sensitivity is similar using both probes, but an advantageous 200% increase in maximum fluorescence is obtained on average when using the double-stranded probe according to the invention.

Lastly, this experiment also shows that the gain of fluorescence obtained by using double stranded probe is independent of the polymerase used, since the same results were observed with five different commercial polymerases, whether chemically modified or not.

The invention claimed is:

1. A double-stranded probe intended for the fluorescent detection of a single-stranded or double-stranded target nucleic acid, comprising:
   a first strand of formula $X_1$-$L_1$-$S_1$-$S'_1$-$Y_1$, intended for the detection of a first strand of the target nucleic acid which comprises a sequence of formula $T'_1$-$T_1$; and
   a second strand of formula $X_2$-$L_2$-$S_2$-$S'_2$-$Y_2$, intended for the detection of a second strand of the target nucleic acid, if present, said second strand of the target nucleic acid comprising a sequence of formula $T'_2$-$T_2$;
   wherein:
   $X_1$ and $X_2$ represent fluorescent donors and $Y_1$ and $Y_2$ represent a fluorescent acceptors;
   $T_1$ and $T_2$ represent oligonucleotide sequences having from 10 to 35 nucleotides which are complementary to one another;
   independently from one another, $T'_1$ and $T'_2$ represent oligonucleotide sequences having from 2 to 8 nucleotides;
   $S_1$ and $S_2$ represent oligonucleotide sequences having from 10 to 35 nucleotides which are complementary to one another, $S_1$ being at least 85% complementary to $T_1$, and $S_2$ being at least 85% complementary to $T_2$;
   independently from one another, $S'_1$ and $S'_2$, represent oligonucleotide sequences having from 3 to 8 nucleotides, $S'_1$ being at least 65% complementary to $T'_1$, and $S'_2$ being at least 65% complementary to $T'_2$;
   $L_1$ and $L_2$ are spacer moieties such that the respective gyration radius of $X_1$ and $X_2$ with respect to the attachment sites of $S_1$ to $L_1$ and $S_2$ to $L_2$ is at least 3.4 Å, wherein $L_1$ and $L_2$ are polynucleotides, and wherein $L_1$ and $L_2$ have less than 35% complementarity with $S'_2$ and $S'_1$ respectively,
   wherein $L_1$ and $L_2$ are independently selected from the group consisting of a polynucleotide having from 2 to 10 nucleotides, and the length of one or both of $L_1$ and $L_2$ is shorter than that of one or both of $S'_2$ and $S'_1$ respectively; and
   a melting temperature of the double-stranded probe is lower than a melting temperature of a complex formed between the first strand of the double stranded-probe and the first strand of the target nucleic acid; and lower than a melting temperature of a complex formed between the second strand of the double stranded-probe and the second strand of the target nucleic acid, if present.

2. The double-stranded probe according to claim 1, wherein the fluorescent donor is selected from the group consisting of xanthene dyes, rhodamine dyes, carbopyronine dyes and carboxamide dyes.

3. The double-stranded probe according to claim 1, wherein the fluorescent acceptor is a dark quencher.

4. The double-stranded probe according to claim 1, wherein $L_1$ and $L_2$ respectively quench less than 25% of the fluorescence of $X_1$ and $X_2$.

5. The double-stranded probe according to claim 1, wherein at least one of $L_1$ and $L_2$ comprise at least one positive charge.

6. The double-stranded probe according to claim 1, wherein one or more of $L_1$ and $L_2$ is a polyT polynucleotide.

7. The double-stranded probe according to claim 1, wherein a melting temperature of the first strand of the probe with respect to the second strand of the probe is at least 10% lower than the melting temperature of either the first strand or the second strand with respect to their respective target nucleic acid strands.

8. The double-stranded probe according to claim 1, wherein said double-stranded probe comprises:
   a first nucleic acid strand of formula $X_1$-$L_1$-$S_1$-$S'_1$-$Y_1$, and
   a second nucleic acid strand of formula $X_2$-$L_2$-$S_2$-$S'_2$-$Y_2$;
   and wherein:
   $X_1$ and $X_2$ are selected from the group consisting of FAM, Atto532, NK141, NK230 and Atto647N;
   $Y_1$ and $Y_2$ represent Dabcyl;
   $L_1$ and $L_2$ represent a polyT polynucleotide having from 3 to 6 nucleotides;
   $S_1$ and $S_2$ represent an oligonucleotide sequence having from 14 to 18 nucleotides; and
   $S'_1$ and $S'_2$ represent an oligonucleotide sequence having from 4 to 6 nucleotides.

9. The double-stranded probe according to claim 8 intended for the detection of *Salmonella typhi*, wherein said double-stranded probe comprises:
   a first nucleic acid strand of formula $X_1$-$L_1$-$S_1$-$S'_1$-$Y_1$, in the 5' to 3' orientation, and
   a second nucleic acid strand of formula $X_2$-$L_2$-$S_2$-$S'_2$-$Y_2$, in the 5' to 3' orientation;
   and wherein:
   $L_1$ and $L_2$ represent 5'-TTT-3' (SEQ ID NO: 86);
   $S_1$ represents 5'-GAATAGTGAGCGTGCCT-3' (SEQ ID NO: 87);
   $S'_1$ represents 5'-TACCG-3' (SEQ ID NO: 88);
   $S_2$ represents 5'-AGGCACGCTCACTATTC-3' (SEQ ID NO: 89); and
   $S'_2$ represents 5'-TGACA-3' (SEQ ID NO: 90).

10. The double-stranded probe according to claim 1, wherein the fluorescent acceptor is 4-(4-dimethylaminophenyl)diazenyl benzoic acid ; 4-N,N -dimethylaminoazobenzene-4' sulfonic acid; Xanthylium, 9-[2-[[4-[[(2,5-dioxo-1-pyrrolidinyl)oxy]carbonyl]-1-piperidinyl]sulfonyl]phenyl]-3,6-bis(methylphenylamino)-, chloride; N-(9-{2-[(4-{[(2,5-dioxopyrrolidin-1-yl)oxy]carbonyl}piperidin-1-yl)sulfonyl]phenyl}-6-[methyl(4-sulfophenyl)amino]-3H-xanthen-3-ylidene)-N-methyl-4-sulfoanilinium; 2-[6-(1,3-dihydro-2H-isoindol-2-yl)-9-{2-[(4-{[(2,5-dioxopyrrolidin-1-yl)oxy]carbonyl}piperidin-1-yl)sulfonyl]phenyl}-3H-xanthen-3-ylidene]-2,3-dihydro-1H-isoindolium chloride; 4-N-methyl-N-(4'nitro-2'-chloroazobenzen-4-yl)-aminobutanamido-1-(2-O-dimethoxytrityloxymethyl)-pyrrolidin -4-yl-succinoyl long chain alkylamino-CPG; 4-dimethylaminophenylazophenyl-4'-maleimid; 4-[(4-dimethylaminophenyl)phenylmethyl]-N,N-dimethylaniline; or 2H-chromen-2-one.

11. A kit intended for the fluorescent detection of a single-stranded or double-stranded target nucleic acid comprising:
   a first nucleic acid strand of formula $X_1$-$L_1$-$S_1$-$S'_1$-$Y_1$ as defined in claim 1; and
   a second nucleic acid strand of formula $X_2$-$L_2$-$S_2$-$S'_2$-$Y_2$ as defined in claim 1.

12. A kit for the fluorescent detection of at least one single-stranded or double-stranded target nucleic acid in an enzyme-based nucleic acid amplification method, comprising:
   at least one double-stranded probe according to claim 1;
   an enzyme for enzyme-based nucleic acid amplification; and
   a reagent mixture adapted for enzyme-based nucleic acid amplification.

13. A kit according to claim 12, further comprising nucleotide primers adapted for enzyme-based amplification of the target nucleic acid.

14. A kit according to claim 12 for the detection of more than one single-stranded or double-stranded target nucleic acid in a multiplex enzyme-based nucleic acid amplification method, said kit comprising more than one double-stranded probe according to claim 1, wherein each of said target nucleic acids is able to be detected by at least one of said double-stranded probes.

\* \* \* \* \*